(12) United States Patent
Napoletano et al.

(10) Patent No.: US 6,589,951 B1
(45) Date of Patent: Jul. 8, 2003

(54) PHTHALAZINE DERIVATIVES AS PHOSPHODIESTERASE 4 INHIBITORS

(75) Inventors: Mauro Napoletano, Milan (IT); Gabriele Norcini, Vizzola Ticino (IT); Daniela Botta, Como (IT); Giancarlo Grancini, Nova Milanese (IT); Gabriele Morazzoni, Lainate (IT); Francesco Santangelo, Milan (IT); Jorge G. Siro Herrero, Calà d'Henares (ES); José Luis Garcia Navaio, Madrid (ES); Julio G. Alvarez-Builla, Madrid (ES)

(73) Assignee: Zambon Group S.p.A., Vincenza (IT)

(*) Notice: Subject to any disclaimer, the term of this patent is extended or adjusted under 35 U.S.C. 154(b) by 0 days.

(21) Appl. No.: 09/581,506

(22) PCT Filed: Dec. 17, 1998

(86) PCT No.: PCT/EP98/08291

§ 371 (c)(1),
(2), (4) Date: Aug. 10, 2000

(87) PCT Pub. No.: WO99/32456

PCT Pub. Date: Jul. 1, 1999

(30) Foreign Application Priority Data

Dec. 19, 1997 (IT) .......................................... MI97A2806

(51) Int. Cl.⁷ ..................... A61K 31/502; C07D 237/30
(52) U.S. Cl. ....................... 514/248; 514/241; 544/180; 544/237

(58) Field of Search .................................. 544/237, 182, 544/180; 514/252, 141, 242, 245, 241, 248

(56) References Cited

FOREIGN PATENT DOCUMENTS

| EP | 2 468 593 A | 5/1981 |
| NL | 8 005 411 | 4/1981 |
| WO | WO97/48697 | * 12/1997 |

* cited by examiner

*Primary Examiner*—John M. Ford
(74) *Attorney, Agent, or Firm*—Arent Fox Kintner Plotkin & Kahn

(57) ABSTRACT

Compounds of formula (I) wherein B is alkylene, amino, CONH or a bond; Cy is optionally substituted phenyl or heteroaryl; R is H, phenyl or $(C_{1-4})$alkyl optionally substituted; $R_1$ is $(C_{1-6})$alkyl or polyfluoro$(C_{1-6})$-alkyl; $R_2$ is $(C_{4-7})$cycloalkyl optionally containing an oxygen atom and optionally substituted; and the N→O derivatives and pharmaceutically acceptable salt thereof are PDE 4 and TNFα inhibitors.

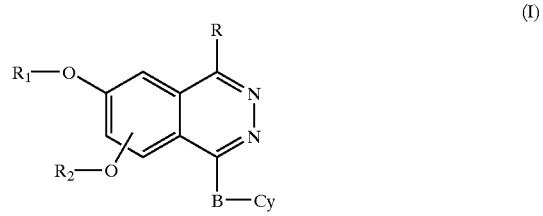

(I)

8 Claims, No Drawings

PHTHALAZINE DERIVATIVES AS PHOSPHODIESTERASE 4 INHIBITORS

This is a 371 of International Application Serial No. PCT/EP98/08291, filed Dec. 17, 1998.

The present invention relates to phthalazine derivatives, to pharmaceutical compositions comprising them and to their use as phosphodiesterase 4 inhibitors.

Phosphodiesterases are a family of isoenzymes which constitutes the basis of the main mechanism of cAMP (cyclic adenosine-3',5'-monophosphate) hydrolytic inactivation. cAMP has been shown to be the second messenger mediating the biologic response to many hormones, neurotransmitters and drugs [Krebs Endocrinology Proceedings of the 4th International Congress Excerpta Medica, 17–29, 1973]. When the suitable agonist binds the cell surface, the adenylated cyclase activates and turns $Mg^{2+}$-ATP into cAMP. cAMP modulates the activity of the majority, if not of all, of the cells contributing to the pathophysiology of various respiratory diseases both of allergic origin and not. It follows that an increase of CAMP concentration yields beneficial effects such as airway smooth muscle relaxation, inhibition of the mast cell mediator release (basophil granulose cells), suppression of the neutrophil and basophil degranulation, inhibition of the monocyte and macrophage activation. Thus, compounds capable of activating adenylate cyclase or of inhibiting phosphodiesterases could suppress the undesired activation of the airway smooth muscle and of a great number of inflammatory cells.

In the phosphodiesterase family there is a distinct group of isoenzymes, phosphodiesterases 4 (hereinafter PDE 4), specific for the hydrolysis of the airway smooth muscle and inflammatory cells cAMP (Torphy, "Phosphodiesterase Isoenzymes: Potential Targets for Novel Anti-asthmatic Agents" in New Drugs for Asthma, Barnes, ed. IBC Technical Services Ltd, 1989). Studies carried out on this enzyme show that its inhibition yields not only airway smooth muscle relaxation, but also mastocyte suppression, basophil and neutrophil degranulation, thus inhibiting monocyte activation and neutrophil activation. Furthermore, the PDE 4 inhibitors activity is markedly improved when the adenylated cyclase activity of the target cells is enhanced by endogenous hormones, as the case in vivo. Thus, PDE 4 inhibitors should be effective in the therapy of asthma. Such compounds would offer a unique approach to the therapy of various respiratory diseases both of allergic origin and not, and possess significant therapeutic advantages over the current therapy.

The excessive or irregular production of the tumor necrosis factor (hereinafter $TNF_\alpha$), a cytokine with pro-inflammatory activity produced by various kind of cells, affects the mediation or the exacerbation of many pathologies such as, for example, the adult respiratory disease syndrome (ARDS) and the chronic pulmonary inflammatory disease. Therefore, compounds able to control the negative effects of $TNF_\alpha$, i.e. the inhibitors of this cytokine, are to be considered useful against many pathologies.

The patent application EP-0 722 936 (in the name of Eisai) claims, inter alia, compounds of formula

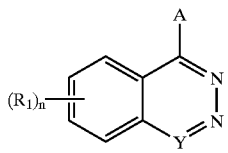

wherein n=0–4; $R_1$, is an optionally substituted lower alkoxy or cycloalkyl, or a —$OR_9$ group wherein $R_9$ is an optionally substituted arylalkyl group; Y is —CB═ wherein B is an optionally substituted heteroarylalkyl group or —$NR_7R_8$ wherein one of $R_7$, and $R_8$ may be H and the other an optionally substituted heteroarylalkyl group; A is hydrogen or a halogen atom, optionally mono- or bi-substituted amino group, optionally substituted aryl, heteroaryl or heteroarylalkyl group. Among the groups optionally substituting the above mentioned residues halogen atoms are listed. Such compounds are said to be active as cGMP-PDE inhibitors, i.e. PDE 5, a phosphodiesterase acting by a cGMP-dependent mechanism and whose field of action is markedly cardiovascular (Schudt C. et al., Phosphodiesterase Inhibitors, Academic Press).

The patent application EP0 498 723 (in the name of Roussel Uclaf) discloses, inter alia, compounds of formula

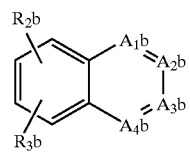

wherein $R_2b$ and $R_3b$ are hydrogen, hydroxy, alkyl, cycloalkyl, acyloxy, at least one but no more then two of $A_1b, A_2b, A_3b$ and $A_4b$ are a nitrogen atom and at least one of them is a methyne radical substituted by the —$R_5$—$Y_B$ group wherein $R_5$ is a divalent alkylene radical, and $Y_B$ represents the radical —$Y_{1B}$—B—$Y_{2B}$ wherein $Y_{1B}$ is a monocyclic aryl optionally containing nitrogen, B is a single bond and $Y_{2B}$ is hydrogen or halogen. These compounds are said to be effective for the treatment of arterial hypertension, heart and renal failure and for the prevention of restenosis after angioplasty.

The patent application EP-0 017 411 (in the name of Pfizer) claims phthalazines of formula

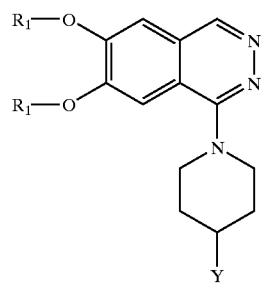

wherein $R_1$ is lower alkyl; Y is —$(CH_2)_m$—Z wherein m is 1 or 2, and Z is carbamoyloxy, carbonylamino, sulfamoyl, ureido, amino-sulfamoyl, carboxamino substituted on the terminal portion by a $(C_{3-7})$cycloalkyl. These compounds are said to be phosphodiesterase inhibitors and to have a cardiac muscle stimulating activity, thus their action does not relate to PDE 4. The U.S. Pat. No. 3,274,185 (in the name of Messengill) describes, inter alia, phthalazines of formula

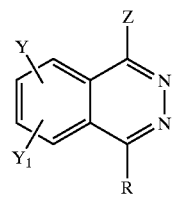

wherein Y and $Y_1$ are lower alkoxy; Z is phenyl optionally substituted by halogen or benzyl; and R is hydrogen. These phthalazines are endowed with sedative and hypertensive activity, without an explicit mechanism of action.

The U.S. Pat. No. 3,813,384 (in the name of Asta-Werke) illustrates, inter alia, benzylphthalazinones of formula

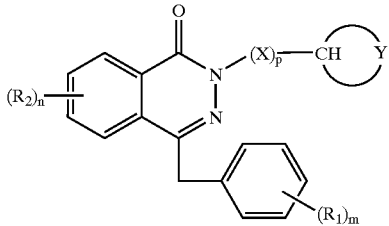

wherein $R_1$ and $R_2$ are lower alkoxy or halogen; X is an optionally branched alkylene chain; m and n are 1–3; p is 0 or 1; and the

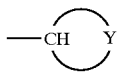

group is a $C_{3-8}$ mono-, bi- or tricyclic residue containing one or two nitrogen atom(s). Such compounds have a hystaminolytic action and are useful, for example, in the treatment of asthma.

The patent application NL 8005411 (in the name of Mitsubishi Yuka) describes phthalazines of formula

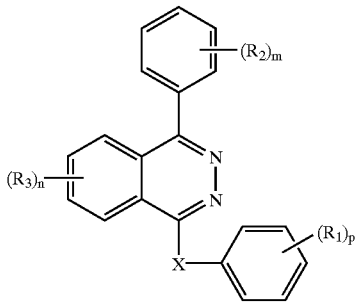

wherein X is O or NH, $R_1$, $R_2$ and $R_3$ are, inter alia, $(C_{1-5})$alkyl, $(C_{1-5})$alkoxy, halogen or $CF_3$; n, m and p are 0–3. The use of these compounds is as platelet aggregation inhibitors.

The patent application JP-56061365 (in the name of Showa Denko) describes phthalazinones of formula

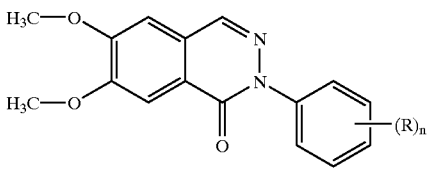

wherein, inter alia, R is halogen and n is 1–3, as vasodilators and anti-ulcer agents.

The patent application WO 97/40020 (in the name of Schering AG) illustrates, inter alia, compounds of formula

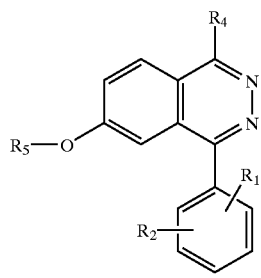

wherein $R_1$ and $R_2$ are H, nitro, halogen, amino, lower alkoxy or —$CF_3$; $R_4$ is H or lower alkyl; $R_5$ is lower alkyl. These compounds are uncompetitive antagonists of excitatory aminoacids. The patent application WO097/48697 (in the name of Rhone Poulenc Rorer), published on Dec. 24, 1997, disloses, inter alia, compounds of formula

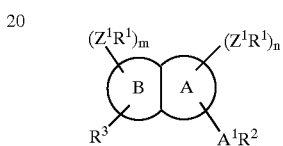

wherein A is an azaheterocycle and B an azaheteroaryl ring or an optionally halo-substituted benzene ring; $Z^1$ is a bond or an oxygen atom; $R^1$ is H or lower alkyl optionally substituted by halogen atom(s); $A^1$ is a bond or a $C_{1-6}$ alkylene optionally substituted by aryl, cycloalkyl or heteroaryl; $R^2$ may be H, aryl heteroaryl; $R^3$ may be aryl, heteroaryl, aryl-methoxy, heteroaryl-methoxy; n and m are alternatively 0 or 1. The aryl and heteroaryl moieties may be substituted by halogen atoms. These compounds are PDE 4 and TNF inhibitors.

Therefore the present invention relates to compounds of formula I

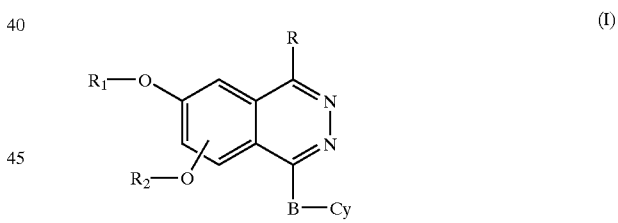

wherein B is methylene, ethylene, amino, CONH or a bond;
Cy is phenyl or a 5- or 6-membered heterocycle containing from 1 to 3 nitrogen atom(s), being both the residues optionally substituted by one or more substituent(s);
R is H, phenyl or a $(C_{1-4})$alkyl group optionally substituted by an aromatic or hydrogenated ring containing from 5 to 7 members;
$R_1$ is a $(C_{1-6})$alkyl or polyfluoro$(C_{1-6})$alkyl group;
$R_2$ is aryl aryl-$(C_{1-10})$alkyl or a $(C_{4-7})$cycloalkyl group optionally containing an oxygen atom and optionally substituted by a polar substituent;
and the N→O derivatives and pharmaceutically acceptable salts thereof;
with the proviso that when R is H, $R_2$ is not aryl-methyl.

The proviso is due to avoid the overlap with the patent application WO97/48697 (in the name of Rhone Poulenc Rorer) said above.

The compounds of formula I may have an asymmetric centre and thus may be in the form of stereoisomers. The objects of the present invention are the compounds of formula I in the form of stereoisomeric mixtures as well as single stereoisomers.

The compounds of formula I are active as PDE 4 and $TNF_\alpha$ inhibitors, and are thus used as therapeutic agents in allergic and inflammatory pathologies such as, for example, emphysema, chronic bronchitis, asthma and allergic rhinitis.

As for 5- or 6-membered heterocycle it is meant pyrrole, imidazole, pyrazole, pyrrolidine, pyrroline, imidazoline, imidazolidine, pymzolidine, pyrazoline, pyridine, pyrazine, pyrimidine, pyridazine, piperazine, piperidine, triazine, and the like, preferably pyridine and piperidine. The substituents optionally present on Cy may be keto, nitro, carboxy, halogen, this term embracing a fluorine, chlorine, bromine or iodine atom, chlorine being the preferred substituent.

Specific examples of alkyl groups are methyl, ethyl, n-propyl, i-propyl, n-butyl, s-butyl, tert-butyl, n-pentyl, 1-methyl-butyl, 2-ethyl-propyl, 3-ethyl-utyl, 3-ethyl-tyl, n-exyl and the like. As for $(C_{5-7})$ cycloalkyl group it is meant cyclopentyl, cyclohexyl and cycloheptyl, and when it contains an oxygen atom it is meant, for example, tetrahydrofuran or tetrahydropyran, while aryl and aryl-$(C_{1-10})$ mean a ring or a $C_{6-10}$ aromatic system such as, for example, phenyl, benzyl, phenethyl, phenyl-pentyl, naphthyl, indanyl, indanyl-pentyl and the like. For "polar substituent" it is meant those groups constituted by atoms with different electronegativity thereby a dipole is created, such as, for example, hydroxy or keto groups, are meant.

The N→O groups optionally preset in number of one or more may regard both the nitrogen atoms of the phthalazine ring, and the ones on the substituent Cy.

Pharmaceutically acceptable salts of the compounds of formula I are those with organic and inorganic acids, such as, for example, hydrochloric, hydrobromic, hydroiodic, nitric, sulfuric, phosphoric, acetic, benzoic, maleic, fumaric, succinic, tartaric, citric, aspartic, methansulfonic, 3,7-di-tert.butylnaphthalen-1,5-disulfonic (dibudinic acid).

Preferred compounds of formula I are those wherein B is methylene or amino; Cy is phenyl or a 5- or 6membered heterocycle containing from 1 to 3 nitrogen atom(s), both the residues being optionally substituted by 1 or 2 halogen(s); R is H, phenyl or a $(C_{1-4})$alkyl group optionally substituted by an aromatic or hydrogenated ring containing 5–7 members; $R_1$ is a $(C_{1-6})$alkyl or polyfluoro$(C_{1-6})$alkyl group; $R_2$ is a $(C_{4-7})$cycloalkyl group optionally containing an oxygen atom and optionally substituted by a polar substituent; and the N→O derivatives and pharmaceutically acceptable salts thereof.

More preferred compounds of formula I are those wherein B is methylene; Cy is phenyl or a 6-membered heterocycle containing 1 nitrogen atom, being both the residue substituted by 1 or 2 chlorine atom(s); R is phenyl or a $(C_{1-4})$alkyl group optionally substituted by a 5–7 members aromatic or hydrogenated ring; $R_1$ is a $(C_{1-6})$alkyl, polyfluoro$(C_{1-6})$-alkyl group; $R_2$ is a $(C_{4-7})$-cycloalkyl group optionally containing an oxygen atom and optionally substituted by a polar substituent; and the N→O derivatives and the pharmaceutically acceptable salts thereof.

The synthesis of the compounds of formula I proceeds according to methods known to the skilled in the art. For example, a benzaldehyde of formula II

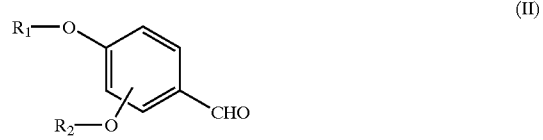

wherein $R_1$ and $R_2$ are as defined above, is oxidized, for example with potassium permanganate and tetrabutylammonitun bromide, to give an acid of formula III

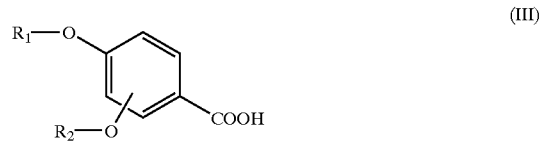

wherein $R_1$ and $R_2$ are as defined above, which, for example by treatment with thionyl chloride, is turned into the corresponding acyl halide of formula IV

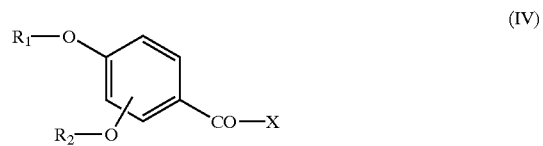

wherein $R_1$ and $R_2$ are as defined above and X is chlorine or bromine. This compound is reacted with diethylamine in an at least equimolar amount to give a benzamide of formula V

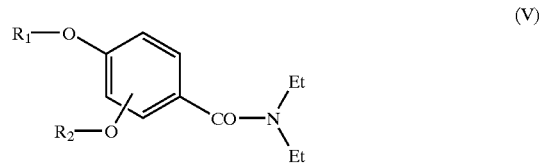

wherein $R_1$ and $R_2$ are as defined, which reacted with dimethylformamide in the presence of a strong organic base such as, for example, n-butyl-lithium, tert butyl-lithium, sec-butyl-lithium, optionally in the presence of a binding agent such as, for example, tetramethylethylendiamine, yields a compound of formula VIa

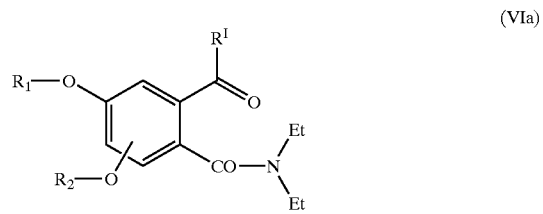

wherein $R_1$ and $R_2$ are as defined above, and $R^1$ is hydrogen.

When a compound of formula I wherein R=H is desired, the compound of formula VIa is reacted with an equimolar amount of tert-butylcarbazole to give a compound of formula VIIa

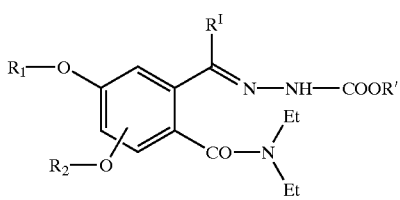

(VIIa)

wherein $R^1$, $R_1$ and $R_2$ are as defined above, and R' is a protecting group of the carboxy moiety such as, for example, tert-butyl.

Instead, when a compound of formula I wherein R is other than hydrogen is desired, the compound of formula VIa is treated with $R''$-magnesium halide, for example, chloride, or $R''$-lithium, wherein $R''$ is phenyl or a $(C_{1-4})$alkyl group optionally substituted by an aromatic or hydrogenated ring having from 5 to 7 members, to give a compound of formula XIII

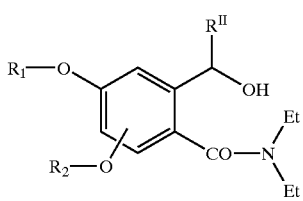

(XIII)

wherein $R''$, $R_1$ and $R_2$ are as defined above. The compound of formula XIII is treated with a suitable oxidising agent such as, for example, pyridinium-chloro chromate, and yields a compound of formula VIb

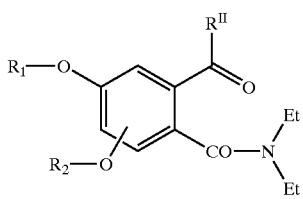

(VIb)

wherein $R_1$, $R_2$ and $R''$ are as defined above, which is treated with an equimolar amount of tert.butylcarbazole to give a compound of formula VIIb, which differs from the compound VIIa in that R has the meanings of formula I but hydrogen.

The compound of formula VIIa or VIIb is reacted with trifluoroacetic acid to give the phthalazinone of formula VIII

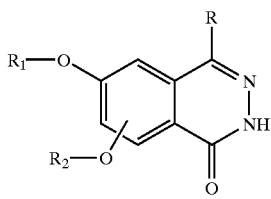

(VIII)

wherein R, $R_1$ and $R_2$ are as defined above. This phthalazinone is reacted with a halogenating agent such as, for example, phosphoryl chloride, to give the phthalazine of formula IX

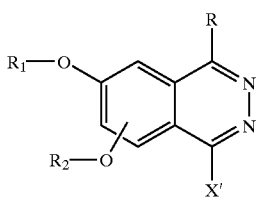

(IX)

wherein R, $R_1$ and $R_2$ are as defined above, and X' is a halogen atom.

Alternatively, the compound of formula VIII may be directly obtained from the compound of formula VIa or VIb by treatment with hydrazine in acetic acid.

The compound of formula IX yields a compound of formula I by treatment with a compound of formula XIV $$Cy—B'—Y \qquad (XIV)$$

wherein Cy is as defined above, B' is methylene, ethylene, amino or a bond and Y is hydrogen, halogen.

When a compound of formula I wherein B is CONH is desired, the compound IX is reacted with carbon monoxide and methanol in the presence of a catalyst such as metal palladium or nickel, to give a compound of formula XV

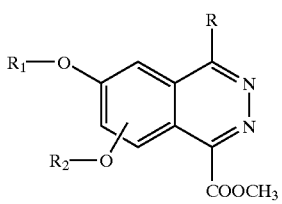

(XV)

wherein R, $R_1$, and $R_2$ are as defined above, which is then turned into the desired compound of formula I through methods known to those skilled in the art, for example by reaction with an aryl-amine in the presence of bases.

Alternatively, the compounds of formula I may be synthesized by treatment of a compound of formula VIa or VIb with acetic acid in acidic medium to give a compound of formula X

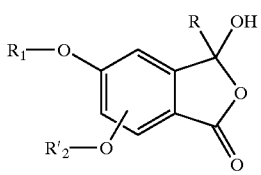

(X)

wherein R and $R_1$ are as defined above, and $R'_2$ has the meaning of $R_2$ listed above plus hydrogen, which is reacted with hydrazine to give a phthalazinone of formula XI

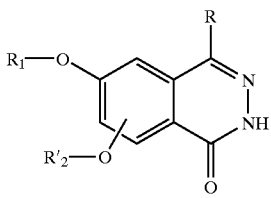

(XI)

wherein R, $R_1$ and $R'_2$ are as defined above. When $R'_2$ is hydrogen this compound is treated with the due compound of formula XIIa or XIIb $R_2OSO_2CH_3$ (XIIa)

$R_2X$ (XIIb)

wherein $R_2$ and X are as defined above to give a compound of formula VIII as described above.

Another alternative is for the compounds of formula I wherein B is other than amino, which may be yielded starting from the acid of formula III reacted with formaldehyde/HCl which forms a compound of formula XVI

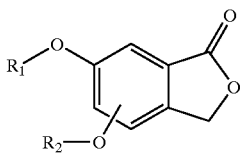

(XVI)

wherein $R_1$ and $R_2$ are as defined above. This compound is oxidized, for example with benzoyl peroxide/N-bromo-succinimide, then hydrolyzed to give a compound of formula XVII

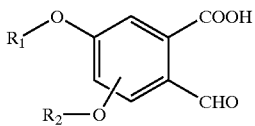

(XVII)

wherein $R_1$ and $R_2$ are as defined above, which with a halogenidric acid and triphenylphosphine gives a compound of formula XVIII

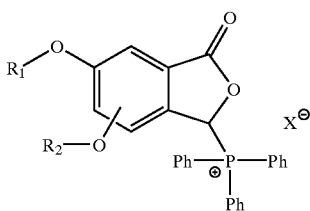

(XVIII)

wherein $R_1$ and $R_2$ are as defined above, which treated with an aldehyde of formula XIX Cy—B"—CHO (XIX)

wherein Cy is as defined above and B" is methylene or is absent, in the presence of an organic base such as, for example, triethylamine, gives a compound of formula XX

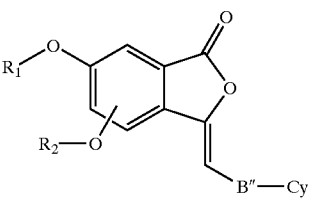

(XX)

wherein $R_1$, $R_2$, B" and Cy are as defined above. This is reacted with hydrazine to give a compound of formula XXI

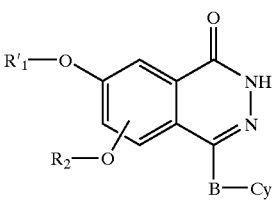

(XXI)

wherein $R_1$, $R_2$, and Cy are as defined above and B is other than amino, which is treated with a halogenating agent, such as phosphoryl chloride or bromide, to give a compound of formula XXII

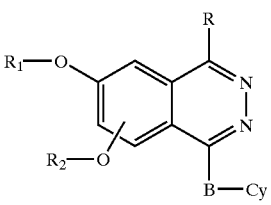

(XXII)

wherein $R_1$, $R_2$, X and Cy are as defined above and B is other than amino. This compound is subjected to a coupling reaction with the suitable metallorganic derivative in the presence of a catalyst, for example, a palladium-based catalyst, or to a nucleophilic substitution which gives a compound of formula I wherein B is other than amino.

A choice for having a compound of formula I wherein $R_1$ is a polyfluoro($C_{1-6}$)alkyl group consists in treating a compound of formula XXIII

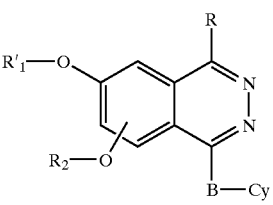

(XXIII)

wherein $R'_1$, is hydrogen, with bases, for example a carbonate or bicarbonate, and a polyfluoro($C_{1-6}$)alkyl-chloride, -bromide or -iodide at 70–75° C. The compound of formula XXIII may be obtained from a compound of formula I wherein $R_1$ is ($C_{1-6}$)alkyl for example by treatment with sodium p-thiochresolate in the presence of a base such as dimethylformamide.

The synthesis of the N-oxides of the compounds of formula I is effected by treating the compounds of formula I with peracids such as, for example m-chloroperbenzoic acid.

The preparation of the salts of the compounds of formula I is effected by conventional methods.

The compounds of formula I are PDE 4 inhibitors as resultant from the in vitro enzymatic inhibition activity tests (Example 67), without any effect on PDE 3 and PDE 5 (Example 69). Moreover they are able to inhibit the $TNF_\alpha$ release (Example 68). Companions with the following compounds have been carried out: 6,7-dimethoxy-4-(pyridin-4-yl-methyl)-2H-phthalazin-1-one (reference 1) and 6,7-dimethoxy-4-(piperidin-4yl-methyl)-2H-phthalazin-1-one (reference 2) embraced by the general formula of the patent application EP-0 722 936 (in the name of Eisai) just cited above, chosen in view of the structural affinity with the compounds of the invention. The reference compounds, though chemically alike, did not show to be active on PDE 4.

It is apparent how these receptorial selectivity and specificity features joined with the lack of activity on the cardiovascular system make the compounds of formula I particularly suitable for the treatment of the pathologies involving PDE 4 and $TNF_\alpha$ even if in the present context the interest is specifically focused on the respiratory pathologies. Especially the compounds of the invention are useful in the treatment of allergic and inflammatory diseases and above all in the therapy of emphysema, of chronic obstructive pulmonary disease and chronic bronchitis in particular, of asthma and allergic rhinitis.

The therapeutical dosage shall generally be comprised between 0.1 and 1,000 mg a day and between 1 and 100 mg by oral route for a single administration.

A further object of the present invention are the pharmaceutical compositions comprising a therapeutically effective amount of the compounds of formula I or of the pharmaceutically acceptable salts thereof in admixture with a suitable carrier.

The pharmaceutical compositions object of the invention may be liquid, suitable for enteral or parenteral administration, and, preferably, solid such as tablets, capsules, granulates, suitable for oral admin on, or in a form suitable for the transdermic or inhalatory administration. The preparation of the pharmaceutical compositions object of the invention may be effected according to common techniques.

Provided below are examples in order to better illustrate the present invention.

EXAMPLE 1

Synthesis of 3-Cyclopentyoxy-4-methoxy Benzoic Acid

A solution of potassium permanganate (53.1 g, 0.336 moles) in water (1 l) was added under stirring with a solution of bromide tetrabutylamnonium (111.68 g, 0.336 moles) in water (0.4 l). The formed solid was isolated by filtration, washed with water and dissolved in pyridine (0.5 l). The solution was dropped into a solution of crude 3-cyclopentyloxy-4-methoxy benzaldehyde (obtained as described in J. Med. Chem., 1995, 38, page 4851) (74 g, 0.336 moles) in pyridine (0.2 l) under stign water/ice. At the end ice (3 l) was added and the whole was acidified by dropping 12N HCl (0.85 l). The stirng was kept on for 1.5 hours more, then the solid was isolated by filtration and extraced under ftiing for 30 minutes in ethyl acetate (2 l). The solid residue was removed and the mother liquor was further extracted in ethyl acetate (2×0.7 l). The organic phases were washed with water, anhydrified over sodium sulfate and brought to a small volume to give 53.2 g of the title product (yield: 67%).

$^1$H-NMR (200 MHz, $CDCl_3$) δ (ppm): 7.75–6.87 (m, 3H); 4.87–4.79 (m, 1H); 3.90 (s, 3H); 2.08–1.52 (m, 8H).

EXAMPLE 2

Synthesis of 3-Cyclopentyloxy-4-methoxy Benzoic Acid Chloride

A solution of 3-cyclopentyloxy-4-methoxy benzoic acid (53 g, 0.224 moles) obtained as described in example 1, in thionyl chloride (200 ml) was refluxed for 2 hours under nitrogen, then evaporated to dryness and taken up twice in toluene (100 ml) to give 57 g of the title product which was used as such in the next step.

$^1$H-NMR (200 MHz, $CDCl_3$) δ (ppm): 7.81–7.72 (dd, 1H); 7.52–7.50 (d, 1H); 6.91–6.85 (d, 1H); 4.87–4.75 (m, 1H); 3.91 (s, 3H); 2.08–1.50 (m, 8H).

EXAMPLE 3

Synthesis of 3-Cyclopentyloxy-N,N-diethyl-4-methoxy-benzamide

A solution of 3-cyclopentyloxy-4-methoxy benzoic acid chloride (57 g, 0.224 moles) obtained as described in example 2, in methylene chloride (250 ml) was dropwise added at 5–10° C. with diethylamine (69.2 g, 0.672 moles). The mixture was evaporated to dryness, dissolved in ethyl acetate, washed with water, 2% potassium bisulfate, water again and sodium bicarbonate, anhydrified over sodium sulfite and dried. The residue was taken up in petrolatum (250 ml) to give 61.2 g of the title product (yield: 94%).

$^1$H-NMR (200 MHz, $CDCl_3$) δ (ppm): 6.94–6.78 (m, 3H); 4.80–4.70 (m, 1H); 3.82 (s, 3H); 3.50–3.22 (m, 4H); 1.98–1.50 (m, 8H); 1.17 (t broad, 6H).

EXAMPLE 4

Synthesis of 3-Cyclopentyloxy-N,N-diethyl-2-formyl-4-methoxy-benzamide and 5-Cyclopentyloxy-N,N-diethyl-2-formyl-4-methoxy-benzamide A solution of 3-cyclopentyloxy N,N-diethyl-4-methoxy-benzamide (61.2 g, 0.21 moles), obtained as described in example 3, and terramethylethylendiaiuine (34.86 ml, 0.231 moles) in dry tetrahydrofuran (480 ml) was dropwise added under stirring at −75° C. with sec-butyl-lithium (195.76 ml, 0.231 moles) and, after 1 hour at the same temperature, with dimethylformamide (53.66 ml, 0.693 moles). After a further half hour at −75° C., the reaction mixture was poured into a phosphate buffer pH=7, ethyl acetate and concentrated HCl. The extraction was repeated twice with fresh ethyl acetate, then the extract was washed with 5% potassium bisulfate, then with water, then anhydrified over sodium sulfate and dried, the residue was chromatographed over silica gel (eluent petrolatum/ethyl acetate 1:1) to give 23.3 g of the first title product (product A; yield: 35%) and 6.7 g of the second title product (product B: yield: 10%).

Product A: $^1$H-NMR (200 MHz, $CDCl_3$) δ (PPM): 10.44 (s, 1H); 7.09–6.85 (m. 2H); 5.05–4.98 (m, 1H); 3.84 (s, 3H); 3.59–3.47 and 3.05–2.92 (2q, 4H); 1.95–1.52 (m, 8H); 1.28 and 0.95 (2t, 6H).

-continued

Product B: $^1$H-NMR (200 MHz, CDCl$_3$) δ (PPM): 9.86 (s, 1H); 7.3 (s, 1H); 6.73 (s, 1H); 4.87–4.76 (m, 1H); 3.88 (s, 3H); 3.58 and 3.12 (2q, 4H); 2.05–1.52 (m, 8H); 1.26 and 1.02 (2t, 6H).

EXAMPLE 5

Synthesis of N'-(2-Cyclopentyloxy-6-diethylcarbamoyl-3-methoxy-benzylidene)-hydrazincarboxy Acid tert-Butyl Ester A solution of 3-cyclopentyloxy-N,N-diethyl-2-formyl-4-methoxy-benzamide (21.7 g, 0.068 moles) obtained as described in example 4, product A, and tert-butylcarbazole (12.84 g, 0.1 moles) in absolute ethanol (217 ml) was refluxed for 3 hours, then dried, taken up in petrolatum and dried again. The residue was taken up in ethyl ether (100 ml) and petrolatum (0.2 l), then filtered and the mother liquor was dried to give 27.45 g of the title product (yield: 93%).
$^1$H-NMR (200 MHz, CDCl$_3$) δ (ppm): 8.60 (m, 1H); 8.05 (s broad, 1H); 6.87 (s, 2H); 4.87–4.72 (m, 1H); 3.82 (s, 3H); 3.58–3.25 (m, 4H); 190–150 (m, 8H); 1.40 (s, 9H); 1.22–1.06 (2t, 6H).

EXAMPLE 6

Synthesis of 5-Cyclopentyloxy-6-methoxy-2H-phthalazin-1-one

Trifluoroacetic acid (150 ml) was added with N'-(2-cyclopentyloxy-6-diethylcarbamoyl-3-methoxy-benzylidene)-hydrazincarboxy acid tert-butyl ester (27.35 g, 0.063 moles) obtained as described in example 5, under stirring at 5–10° C., then the mixture was stirred for 15 minutes and dried. The residue was dissolved in methylene chloride (750 ml) and left at room temperature for 6 hours, then washed with 5% sodium bicarbonate to alkalinity, then with water, anhydrified over sodium sulfate and dried. The residue was taken up in ethyl ether (0.11) and filtered to give 15.58 g of the title product (yield: 95%).
$^1$H-NMR (200 MHz, CDCl$_3$) δ (ppm): 10.12 (m, 1H); 8.84 (s, 2H); 8.11 and 7.36 (2d, 2H); 5.11–5.01 (m, 1H); 3.98 (s, 3H); 2.00–1.60 (m, 8H).

EXAMPLE 7

Synthesis of 5-Cyclopentyloxy-1-chloro-6-methoxy-2H-phthalazine

A slurry under nitrogen of 5-cyclopentyloxy-6-methoxy-2H-phthalazin-1-one (7.5 g, 28.81 mmoles), obtained as described in example 6, in phosphoryl chloride (30 ml) was heated under stirring to 80° C., then concentrated to dryness, and the residue was dissolved in ethyl acetate and washed with potassium bicarbonate to alkalinity, then with water, anhydrified over sodium sulfate and evaporated to dryness to give 7.95 g of the tide product (yield: 99%).
$^1$H-NMR (200 MHz, CDCl$_3$) δ (ppm): 8.40 (s, 2H); 8.11 and 7.36 (2d, 2H); 5.11–5.01 (m, 1H); 3.98 (s, 3H); 2.00–1.60 (m, 8H).

EXAMPLE 8

Synthesis of 5-Cyclopentyloxy-1-(3,5-dichloropyridin-4-ylmethyl)-6-methoxy-phthalazine (Compound 1)

A solution of 3,5-dichloro-4-methyl-pyridine (13.86 g, 85.56 mmoles) in dry dimethylformamide (100 ml) was added, under nitrogen and stirring, with 55% NaH (3.73 g, 85.56 mmoles). The mixture was stirred for 1 hour then added with a solution of 5-cyclopentyloxy-1-chloro-6-methoxy-2H-phthalazine (7.95 g, 28.52 mmoles), obtained as described in example 7, in dry dimethylfomamide (70 ml). The mixture was left to stand for one night, quenched with water, diluted with water and extracted methyl aceate. The extract was washed with water and anhydrified over Na$_2$SO$_4$, then evaporated to dryness. The residue was flash chromatographed (eluent:petrolatum/ethyl acetate 1:1) to give 6.58 g of the title product (yield: 57%).
$^1$H-NMR (200 MHz, CDCl$_3$) δ (ppm): 8.92 (s, 1H); 8.49 (s, 2H); 7.89 (d, 1H, JHH=9.1 Hz); 7.63 (d, 1H); 5.21–5.14 (m, 1H); 4.86 (s, 2H); 4.03 (s, 3H); 1.98–1.57 (m, 8H).

EXAMPLE 9

Synthesis of 5-Cyclopentyloxy-1-(3,5-dichloropyridin-4-ylmethyl)-6-methoxy-phthalazin-3-oxide (Compound 2)

A solution under stirring of 5-cyclopentyloxy-1-(3,5-dichloropyridin-4-ylmethyl)-6-methoxy-phthalazine (0.1 g, 0.741 mmoles), obtained as described in example 8, in methylene chloride (2 ml), was added with 55% m-chloroperbenzoic acid (255.75 mg, 0.816 mmoles). The mixture was diluted with methylene chloride, washed with a solution of NaHCO$_3$, anhydrified and dried. The residue was flash chromatographed over silica gel (eluent:methylene chloride/ethyl acetate 1:1) and the eluate taken up in ether to give 0.2 g of the title product (yield: 64%).
$^1$H-NMR (200 MHz, CDCl$_3$) δ (ppm): 8.64 (s, 1H); 8.50 (s, 2H); 7.82 (d, 1H, JHH=9 Hz); 7.40 (d, 1H); 5.16–5.09 (m, 1H); 4.79 (s, 2H); 4.02 (s, 3H); 1.92–1.55 (m, 8H).

EXAMPLE 10

Synthesis of 5-Cyclopentyloxy-1-(3,5-dichloropyridin-4-yl-methyl)-6-hydroxy-phthalazine A solution under nitrogen of 5-cyclopentyloxy-1-(3,5-dichloropyridin-4-ylmethyl)-6-methoxy-phthalazine (1.2 g, 2.97 mmoles), obtained as described in example 8, and sodium p-thiochresolate (866 mg, 5.94 mmoles) in dimethylformamide (20 ml), was heated to 90–95° C. for 2 hours. The reaction mixture was left to stand for 1 night, poured into water/ice, filtered, and the precipitate was suspended in 95° ethanol (30 ml) and stirred for 0.5 hour. The resulting solid was separated by filtration, dissolved by refluxing in methanol/chloroform 1:1 (100 ml) and concentrated to small volume to give 410 mg of the title product which were used as such in the next step.
$^1$H-NMR (200 MHz, DMSO) δ (ppm): 10.89 (m, 1H); 9.42 (s, 1H); 8.66 (s, 2H): 8.09 and 7.69 (dd, 2H, JHH=8.9 Hz); 5.23–5.17 (m, 1H); 4.89 (s, 2H); 1.87–1.56 (m, 8H).

EXAMPLE 11

Synthesis of 5-Cyclopentyloxy-1-(3,5-dichloropyridin-4-yl-methyl)-6-difluoromethoxy-phthalazine (Compound 3)

In a solution of 5-cyclopentyloxy-1-(3,5dichloropyridin-4-ylmethyl)6hydroxy-phthalazine (400 mg, 1.025 mmoles), obtained as described in example 10, potassium carbonate (188.4 mg, 1.366 mmoles) and potassium iodide (68.3 mg) in dimethylformamide (20 ml), a stream of chloro difluoro mane was gurgled by heating at 70–75° C. under stirring. After 4.5 hours, the mixture was poured into water, extracted m ethyl acetate, the extract was washed with water, anhydrified over sodium sulfate and dried. The residue was chromatographed on silica gel (eluent:petrolatum/ethyl acetate 7:3) to give an oil which was crystallized from ethyl ether/40–60° petrolatum 1:3 to give 96 mg of the title product (yield: 21%).

$^1$H-NMR (200 MHz, CDCl$_3$) δ (ppm): 9.68 (s, 1H); 8.52 (s, 2H); 7.90 and 7.82 (dd, 2H, JHH=9 Hz); 6.66 (t, H, JHF=73.5 Hz); 5.17–5.10 (m, 1H); 4.90 (s, 2H); 2.02–1.62 (m, 8H).

EXAMPLE 12

Synthesis of 5-Cyclopentyloxy-1-(3,5-dichloropyridin-4-ylamino)-6-methoxy-phthalazine (Compound 4)

A solution of 2,5-dichloro-4-amino-pyridine (5.1 g, 31.4 mmoles) in dry dimethylformamide (100 ml) under nitrogen was added under stirring with 55% sodium hydride (1.37 g, 31.4 mmoles). The mixture was stirred for 1 hour, then dropwise added with a solution of 5-cyclopentyloxy-1-chloro-6-methoxy-2H-phthalazine (1.75 g, 6.28 mmoles) in dry dimethylformamide (20 ml) and the mixture was heated to 100° C. for 2 hours. The whole was poured into water and extracted in ethyl acetate. The e was washed with water and anhydrified over sodium sulfate, tend dried. The residue was taken up in few of methylene chloride, the insoluble was filtered off and the solution dried, the residue was purified by silica gel chromatography (eluent:methylene chloride+1% of methanol) and the crude was chromatographed a second time (eluent:petrolatum/ethyl acetate 7:3) to give 720 mg of the tide product (yield: 22%)

$^1$H-NMR (200 MHz CDCl$_3$) δ (ppm): 9.59 (m, 1H); 8.32 (s, 2H); 8.28 (s, 1H); 8.23 and 7.33 (2d, 2H, JHH=8.9 Hz); 5.11–5.03 (m, 1H); 3.98 (s, 3H); 1.96–1.57 (m, 8H).

EXAMPLE 13

Synthesis of 3-Benzyloxy-4-methoxy Benzoic Acid

A solution of potassium permanganate (24.81 g, 0.157 moles) in water (0.1 l) was added under stirring with a solution of tetrabutylammonium bromide (50.61 g, 0.157 moles) in water (0.2 l). The formed solid was separated by filtration, washed with water, squeezed, then dissolved in pyridine (0.3 l). The solution was dropped into a solution of 3-benzyloxy-4-methoxy benzaldehyde (38.2 g, 0.157 moles) in pyridine (0.15 l) in water bath. After 3 hours the reaction mixture was brought to acidic pH by 1N HCl, the solid was filtered off and the mother liquor extracted more times in methylene chloride. The organic phases were anhydrified and concentrated to dryness and the residue taken up with 1N NaOH and washed with ethyl ether. The aqueous solution was acidified and extracted twice with methylene chloride, brought to dryness, discoloured with TONSIL® and concentrated to small volume. The resulting precipitate was filtered to give 35.869 g of the title product (yield: 88%)

$^1$H-NMR (200 MHz, CDCl$_3$) δ (ppm): 7.78–6.69 (m, 8H); 5.18 (s, 2H); 3.39 (s, 3H).

EXAMPLE 14

Synthesis of 3-Benzyloxy-4-methoxy Benzoic Acid Chloride

Operating analogously to example 2 starting from 3-benzyloxy-4-methoxy benzoic acid (35.86 g, 0.139 moles) obtained as described in example 1, in thionyl chloride (150 ml), 35.01 g of the title product were obtained (yield: 98%).

$^1$H-NMR (200 MHz, CDCl$_3$) δ (ppm): 7.84–6.90 (m, 8H); 5.16 (s, 2H); 3.95 (s, 3H).

EXAMPLE 15

Synthesis of 3-Benzyloxy-N,N-diethyl-4-methoxy-benzamide

Operating analogously to example 3 starting from 3-benzyloxy-4-methoxy benzoic acid chloride (35.01 g, 0.127 moles) obtained as described in example 14, in methylene chloride (200 ml), and diethylamine (131 ml, 92.54 g, 0.127 moles) in methylene chloride (130 ml), 37.65 g of the title product were obtained (yield: 95%)

$^1$H-NMR (200 MHz, CDCl$_3$) δ (ppm): 7.43–6.84 (m, 8H); 5.14 (s, 2H); 3.88 (s, 3H): 3.31 (m, 4H); 1.07 (m, 6H).

EXAMPLE 16

Synthesis of 3-Benzyloxy-N,N-diethyl-2-formyl-4-methoxy-benzamide

A solution of 3-benzyloxy-N,N-diethyl-4-methoxy-benzamide (39.54 g, 126.2 mmoles) obtained as described in example 15, and tetramethylethylendiamine (16.13 g, 138.3 mmoles) in tetrahydrofuran (4.25 l), cooled to −78° C., was dropwise added with 1.21M s-butyl-lithium (115.64 ml, 138.8 mmoles). After 2 hours N,N dimethylfomamide was added (43 ml, 40.59 g, 555 mmoles) and the mixture was left at the same temperature for 4 hours, then 1 night while the temperature arose. The mixture was washed with 0.47M phosphate buffer pH=7 and the organic phases were separated, the aqueous one was extracted in ethyl ether. The organic phases were anhydrified and concentrated to give a solid which was filtered off. The mother liquor was dried and the crude flash chromatographed (eluent:ethyl acetate/petrolatum 1:1) to give 13.76 g of the title product (yield: 32%).

$^1$H-NMR (200 MHz, CDCl$_3$) δ (ppm): 10.22 (s, 1H); 7.36–7.29 (m, 5H); 7.13 and 6.94 (2s, 2H, JHH=8.3 Hz); 5.17 (s, 2H); 3.94 (s, 3H); 3.52 and 2.93 (2q, 4H); 1.26 and 0.93 (2t, 6H).

EXAMPLE 17

Synthesis of 3,4-Dihydroxy-5-methoxy-3H-isobenzofuran-1-one

3-Benzyloxy-N,N-diethyl-2-formyl-4-methoxy-benzamide (11.6 g, 34 mmoles) obtained as described in example 16 was dissolved in 10% HCl and acetic acid (80+80 ml) and the mixture was refluxed for 18 hours. The solvents were evaporated and the crude was taken up in toluene. The solid was washed with ethyl ether and dried to give 6.66 g of the title product (quantitative yield).

$^1$H-NMR (200 MHz, CDCl$_3$) δ (ppm): 9.64 add 7.82 (2s broad, 2H); 7.28–7.16 (m, 2H); 3.89 (s, 3H); 6.53 (s broad, 1H).

EXAMPLE 18

Synthesis of 5-Hydroxy-6-methoxy-2H-phthalazin-1-one 3,4-Dihydroxy-5-methoxy-3H-isobenzofuran-1-one (6.63 g, 34 mmoles) obtained as described in example 17 was dissolved in ethanol (60 ml) and added with 98% hydrazine (8.5 ml). The mixture was heated until limpidity and after 5 minutes the formed precipitate was filtered, treated with 1N HCl. The mother liquor was concentrated more times and the fractions of solid obtained were joined to give 4.65 g of the title product (yield: 72%).

$^1$H-NMR (200 MHz, CDCl$_3$) δ (ppm): 12.33 (m, 1H); 10.06 (s, 1H); 8.36 (s, 1H); 7.68 and 7.49 (2d, 2H, JHH=8.6 Hz); 3.94 (s, 3H).

EXAMPLE 19

Synthesis of Methansulfonic Acid 2,3-Dihydro-1H-inden-2-yl Ester

2-Indanol (5.14 g, 38.3 mmoles) in methylene chloride (20 ml) at 0° C. was added with triethylamine (6.13 ml 4.46 g, 44.1 mmoles) and a solution of mesyl chloride (3.26 ml, 4.83 g, 42.1 mmoles) in methylene chloride (4 ml). The temperature was raised to room value, then the mixture was poured into water and the organic phase separated, washed with water, anhydrified and dried to give 8.12 g of the title product (yield: 99%)

$^1$H-NMR (200 MHz, CDCl$_3$) δ (ppm): 7.27–7.16 (m, 4H); 5.55–5.46 (m, 1H); 3.42–3.18 (m, 4H); 3.00 (s, 3H).

EXAMPLE 20

Synthesis of 5-(Indan-2-yloxy)-6-methoxy-2H-phthalazin-1-one

Methansulfonic acid 2,3-dihydro-1H-inden-2-yl ester (3.31 g, 15.61 mmoles) obtained as described in example 19, in dimethylformamide (12 ml) was treated with Na$_2$CO$_3$ (2.21 g, 20.32 mmoles) and KI in catalytic amount at 90° C. After 1 night at this temperature 5-hydroxy-6-methoxy-2H-phthalazin-1-one (2 g, 10.41 mmoles) obtained as described in example 18 was added and the mixture was left at 90° C. for another night, then poured into 1N HCl, and the precipitate was filtered, tritured in petrolatum and dried to give 2.55 g of the title product (yield: 80%).

$^1$H-NMR (200 MHz, CDCl$_3$) δ (ppm): 12.43 (s, 1H); 7.97 and 7.64 (2d, 2H, JHH=8.8 Hz); 7.72 (s, 1H); 7.30–7.16 (m, 4H); 5.42–5.34 (m, 1H); 3.99 (s, 3H); 3.22–2.99 (m, 4H).

EXAMPLE 21

Synthesis of 1-Chloro-5-(indan-2-yloxy)-6-methoxy-2H-phthalazine 5-(Indan-2-yloxy)-6-methoxy-2H-phthalazin-1-one (2.55 g, 8.3 mmoles) obtained as described in example 20, was suspended, under nitrogen, in phosphoryl chloride (20 ml). The reaction mixture was refluxed for 1 hour then poured into diluted NaOH (pH=8), extracted in methylene chloride, anhydrified and dried. The crude was tritured in petrolatum to give 2.57 g of the title product (yield: 95%).

$^1$H-NMR (200 MHz, CDCl$_3$) δ (ppm): 9.20 (s, 1H); 8.02 and 7.65 (2d, 2H, JHH=8.8 Hz); 7.27–7.17 (m, 4H); 5.58–5.50 (m, 1H); 4.07 (s, 3H); 3.18 (m, 4H).

EXAMPLE 22

Synthesis of 1-(3,5-Dichloro-pyridin-4-methyl)5-(indan-2-yloxy)-6-methoxy-2H-phthalazine (Compound 5)

A solution of 3,5-dichloro-4-methyl-pyridine (3.63 g, 22.4 mmoles) in dimethylformamide (50 ml) was added under stirring with 55% sodium hydride (0.977 g, 67.2 mmoles), then with a solution of 1-chloro-5-(indan-2-yloxy)-6-methoxy-2H-phthalazine (2.44 g, 7.5 mmoles) obtained as described in example 21, in dimethylformamide. After stirring for 1.5 hours the mixture was poured into a buffer at pH=7 and extracted in methylene chloride. The extract was washed with water, anhydrified and evaporated to dryness. The residue was flash chromatographed (eluent petrolatum/ethyl aceate 6:4) to give 1.7 g of the title product (yield: 54%).

1H-NMR (200 MHz, CDCl$_3$) δ (ppm): 9.31 (s, 1H); 8.49 (s, 2H); 7.94 and 7.68 (2d, 2H, JHH=9.1 Hz); 7.27–7.16 (m, 4R); 5.57–5.47 (m, 1H); 4.87 (s, 2H); 4.07 (s, 3H); 3.23–3.20 (m, 4H).

EXAMPLE 23

Synthesis of Methansulfonic Acid 5-Phenyl-pentyl Ester

Operating analogously to example 19 using 5-phenylpentanol (7.18 ml, 7 g, 42.6 mmoles) in methylene chloride (8 ml) and methyl-sulfonyl chloride (3.63 ml, 5.37 g, 46.9 mmoles) in methylene chloride (4 ml), and also using triethylamine (6.82 ml, 4.96 g, 49 mmoles) to adjust the pH after the addition of methyl-sulfonyl chloride, 10.57 g of the title product were obtained after half an hour of reaction (stoichiometric yield).

$^1$H-NMR (200 MHz, CDCl$_3$) δ (ppm): 7.31–7.13 (m, 5H); 4.20 (t, 2H, JHH=6.5 Hz); 2.96 (s, 3H); 2.65–2.57 (m, 2H); 1.83–1.34 (m, 6H).

EXAMPLE 24

Synthesis of 5-(5-Phenyl-pentyl-1-oxy)-6-methoxy-2H-phthalazin-1-one

Operating analogously to example 20 using 5-hydroxy-6-methoxy-2H-phthalazin-1-one 2 g, 10.41 mmoles) obtained as described in example 18, sodium carbonate (2.21 g, 20.82 mmoles), potassium iodide in catalytic amount, methansulfonic acid 5-phenyl-pentyl ester (3.78 g, 15.61 mmoles) obtained as described in example 23, and dimethylformamide (50 ml) under nitrogen, 3.11 g of the tide product were obtained (yield: 88%).

$^1$H-NMR (200 MHz, CDCl$_3$) δ (ppm): 10.19 (s broad, 1H); 8.41 (s, 1H); 8.13 and 7.35 (2d, 2H, JHH=8.8 Hz); 7.30–7.11 (m, 5H); 4.11 (t, 2H, JHH=6.6 Hz); 3.96 (s, 3H); 2.68–2.60 (m, 2H); 1.91–1.45 (m, 6H).

EXAMPLE 25

Synthesis of 1-Chloro-5-(5-phenyl-pentyl-1-oxy)-6-methoxy-phthalazine

Operating analogously to example 21, using 5-(5-phenyl-pentyl-1-oxy)-6-methoxy-2H-phthalazin-1-one (3.05 g, 9.01 mmoles), obtained as described in example 24, and phosphoryl chloride (5 ml) the title product was obtained as a crude which was used as such in the next step.

$^1$H-NMR (200 MHz, CDCl$_3$) δ (ppm): 9.66 (s, 1H); 8.01 and 7.63 (2d, 2H, JHH=9 Hz); 7.30–7.12 (m, 5H); 4.20 (t, 2H, JHH=6.6 Hz); 4.02 (s, 3H); 2.68–2.60 (m, 2H); 1.94–1.47 (m, 6H).

EXAMPLE 26

Synthesis of 1-(3,5-Dichloro-pyridin-4-methyl)-5-(5-phenyl-pentyl-1-oxy)-6-methoxy-phthalazine (Compound 6)

Operating analogously to example 22 and using 1-chloro-5-(5-phenyl-pentyl-1-oxy)-6-methoxy-phthalazine (3.2 g, 9.01 mmoles) obtained as described in example 25, 3,5dichloro-4-methyl-pyridine (4.38 g, 27.03 mmoles), 55% sodium hydride (1.18 g) and dimethylformamide (50 ml), 0.6 g of the title product was obtained.

$^1$H-NMR (200 MHz, CDCl$_3$) δ (ppm): 9.68 (s, 1H); 8.51 (s, 2H); 8.93 and 7.65 (2d, 2H, JHH=9.2 Hz); 7.30–7.12 (m, 5H); 4.88 (s, 2H); 4.21 (t, 2H, JHH=6.6 Hz); 4.03 (s, 3H); 2.68–2.61 (m, 2H); 1.96–1.47 (m, 6H).

EXAMPLE 27

Synthesis of 7-Cyclopentyloxy-6-methoxy-2H-phthalazin-1-one

Operating analogously to example 6 starting from 7-cyclopentyloxy-N,N-diethyl-2-formyl-4-methoxy-benzamide (obtained similarly to the compound of example 4) the title product was obtained (yield: 80%).

$^1$H-NMR (200 MHz, CDCl$_3$) δ (ppm): 10.90 (s, 1H); 8.03 (s, 1H); 7.72 (s, 1H); 7.00 (s, 1H); 4.96 (m, 1H); 3.98 (s, 3H); 2–18–1.60 (m, 8H).

EXAMPLE 28

Synthesis of 7-Cyclopentyloxy-1-chloro-6-methoxy-2H-phthalazine

Operating analogously to example 7 starting from 7-cyclopentyloxy-6-methoxy-2H-phthalazin-1-one, obtained as described in example 27, the tide product was obtained (yield: 98%).

$^1$H-NMR (200 MHz, CDCl$_3$) δ (ppm): 9.21 (s, 1H); 7.42 (s, 1H); 7.13 (s, 1H); 5.00 (m, 1H); 4.02 (s, 3H); 2.20–1.60 (m, 8H).

EXAMPLE 29 cl Synthesis of 7-Cyclopentyloxy-1-(3,5-dichloropyridin-4-ylmethyl)-6-methoxy-phthalazine (Compound 7)

Operating analogously to example 8 using 7-cyclopentyloxy-1-chloro-6-methoxy-2H-phthalazine, obtained as described in example 28, the title product was obtained (yield: 59%).

$^1$H-NMR (200 MHz CDCl$_3$) δ (ppm): 9.20 (s, 1H); 8.49 (s, 2H); 7.28 (s, 1H); 7.14 (s, 1H); 4.97 (m, 1H); 4.83 (s, 2H); 4.02 (s, 3H); 2.18–1.60 (m, 8H).

EXAMPLE 30

Synthesis of 7-Cyclopentyloxy-1-(3,5-dichloropyridin-4-ylamino)-6-methoxy-phthalazine (Compound 8)

Operating analogously to example 12 using 7-cyclopentyloxy-1-chloro-6-methoxy-2H-phthalazine, obtained as described in example 28, the title product was obtained (yield: 28%).

$^1$H-NMR (200 MHz, CDCl$_3$) δ (ppm): 9.40 (s broad, 1H); 8.36 (s, 2H); 7.90 (s, 1H); 7.83 (s, 1H); 6.95 (s, 1H), 3.00 (m, 1H); 3.98 (s, 3H); 2.20–1.50 (m, 8H).

EXAMPLE 31

Synthesis of N,N-Diethyl-5-cyclopentyloxy-2-(1-hydroxyethyl)-4-methoxybenzamide

A solution of 5-cyclopentyloxy-N,N-diethyl-2-formyl-4-methoxy-benzamide (3.2 g, 10 mmoles), obtained as described in example 4, product B, in dry tetrahydrofuran (50 ml) at 0° C., was dropwise added with a 3M solution of methyl-magnesium chloride (4 ml, 12 moles) in tetrahydrofuran. The mixture was stirred at room temperature for 1 hour, then carefully poured into a mixture of ethyl aceate (0.1 l) and water (0.2 l) and cooled to 3° C. The organic phase was washed with water, anhydrified over Na$_2$SO$_4$ and dried at reduced pressure to give a residue which was chromatographed on silica gel (eluent:ethyl acetate/hexane 1:1) to give 2.7 g of the title product (yield: 80%).

$^1$H-NMR (200 MHz, CDCl$_3$) δ (ppm): 7.40 (s, 1H); 6.82 (s, 1H); 5.41 (q, 1H); 4.86 (m, 1H); 4.01 (q, 2H); 3.93 (s, 3H); 3.55 (q, 2H); 2.18–1.70 (m, 8H); 1.58 (d, 3H); 1.40–1.10 (m, 6H).

EXAMPLE 32

Synthesis of N,N-Diethyl-5-cyclopentyloxy-2-(1-hydroxypropyl)-4methoxy-benzamide Operating analogously to example 31 using 5-cyclopentyloxy-N,N-diethyl-2-formyl-4-methoxy-benzamide, obtained as described in example 4, product B, and ethyl-magnesium bromide the title product was obtained (yield 76%).

$^1$H-NMR (200 MHz, CDCl$_3$) δ (ppm): 7.53 (s, 1H); 6.81 (s, 1H); 5.43 (t, 1H); 4.85 (m, 1H); 4.08 (q, 2H); 3.95 (s, 3H); 3.75 (q, 2H); 2.33 (m, 2H); 2.20–1.60 (m, 8H); 1.51–1.10 (m, 9H).

EXAMPLE 33

Synthesis of N,N-Diethyl-5-cyclopentloxy-4-methoxy-2-(1-oxoethyl)-benzamide

A solution of N,N-diethyl-5-cyclopentyloxy-2(1-hydroxyethyl)-4-methoxybenzamide (2 g, 6 mmoles) obtained as described in example 31, in CH$_2$Cl$_2$ (25 ml) at 10° C. was added with pyridinium-chloro-chromate (1.9 g, 9 mmoles), and the mixture was stirred at room temperature for 1 night, then added with ethyl ether (50 ml) and the residue was washed with ethyl ether (30 ml). The joined solutions were evaporated at reduced pressure and the residue chromatographed on silica gel (eluent:hexane/ethyl acetate 6:4) to give 1.5 g of the title product (yield: 77%).

$^1$H-NMR (200 MHz, CDCl$_3$) δ (ppm): 7.6 (s, 1H); 6.87 (s, 1H); 4.9 (m, 1H); 4.1 (q, 2H); 4 (s, 3H); 3.76 (q, 2H); 2.5 (s, 3H); 2.2–1.6 (m, 8H); 1.4–1.1 (m, 6H).

EXAMPLE 34

Synthesis of N,N-Diethyl-5-cyclopentyloxy-4-methoxy-2-(1-oxopropyl)-benzamide

Operating analogously to example 33 starting from N,N-diethyl-5-cyclopentyloxy-2-(1-hydroxypropyl)-4-methoxy-benzamide, obtained as described in example 32, the title product was obtained (yield: 82%).

$^1$H-NMR (200 MHz, CDCl$_3$) δ (ppm): 7.58 (s, 1H); 6.85 (s, 1H); 4.85 (m, 1H); 4.15 (q, 2H); 3.96 (s, 3H); 3.74 (q, 2H); 3.42 (q, 2H); 2.20–1.60 (m, 8H); 1.53 (t, 3H); 1.40–1.10 (m, 6H).

EXAMPLE 35

Synthesis of 7-Cyclopentyloxy-4-methyl-6-methoxy-2H-phthalazin-1-one

Operating analogously to example 6 using N,N-diethyl-5-cyclopentyloxy-4-methoxy-2-(1-oxoethyl)-benzamide obtained as described in example 33, the title product was obtained.

EXAMPLE 36

Synthesis of 7-cyclopentyloxy-4-ethyl-6-methoxy-2H-phthalazin-1-one

Operating analogously to example 6 using from N,N-diethyl-5-cyclopentyloxy-4-methoxy-2-(1-oxopropyl)-benzamide, obtained as described in example 34, the title product was obtained.

EXAMPLE 37

Synthesis of 1-Chloro-7-cyclopentyloxy-4-methyl-6-methoxy-phthalazine

Operating analogously to example 7 starting from 7-cyclopentyloxy-4-methyl-6-methoxy-2H-phthalazin-1-one, obtained as described in example 35, the tide product was obtained.

EXAMPLE 38

Synthesis of 1-Chloro-7-cyclopentyloxy-4-ethyl-6-methoxy-phthalazine

Operating analogously to example 7 starting from 7-cyclopentyloxy-4-ethyl-6-methoxy-2H-phthalazin-1-one, obtained as described in example 36, the title product was obtained.

EXAMPLE 39

Synthesis of 7-Cyclopentyloxy-1-(3,5-dichloro-pyridin-4-ylmethyl)-4-methyl-6-methoxy-phthalazine (Compound 9)

Operating analogously to example 8 starting from 1-chloro-7-cyclopentyloxy-4-methyl-6-methoxy-phthalazine, obtained as described in example 37, the title product was obtained.

$^1$H-NMR (300 MHz, CDCl$_3$) δ (ppm): 8.50 (s, 2H); 7.30 (s, 1H); 7.23 (s, 1H); 5.04–5.00 (m, 1H); 4.82 (s, 2H); 4.05 (s, 3H); 2.88 (s, 3H); 2.10–1.81 (m, 6H); 1.80–1.60 (m, 2H).

EXAMPLE 40

Synthesis of 7-Cyclopentyloxy-1-(3,5-dichloro-pyridin-4-ylmethyl)-4-ethyl-6-methoxy-phthalazine (Compound 10)

Operating analogously to example 8 using 1-chloro-7-cyclopentyloxy-4-ethyl-6-methoxy-phthalazine, obtained as described in example 38, the tide product was obtained.

$^1$H-NMR (300 MHz, CDCl$_3$) δ (ppm): 8.50 (s, 2H); 7.32 (s, 1H); 7.29 (s, 1H); 5.01–5.05 (m, 1H); 4.81 (s, 2H); 4.05 (s, 3H); 3.26 (q, 2H, J=7.5 Hz); 2.13–1.67 (m, 8H); 1.48 (t, 3H, J=7.5 Hz).

EXAMPLE 41

Synthesis of Methansulfonic Acid Tetrahydro-pyran-2-ylmethyl Ester

A solution of (tetrahydropyran-2-yl)methanol (6 g, 51.65 moles) in methylene chloride (80 ml) at 0° C. was added with triethylamine (8.27 ml, 59.4 moles) then with mesyl chloride (4.4 ml, 56.8 moles) in methylene chloride (5 ml). The temperature was left to rise to room value and after 30 minutes the mixture was poured into water and extracted in methylene chloride. The organic phases were anhydrified and dried to give 10 g of the title product (quantitative yield).

EXAMPLE 42

Synthesis of 6-Methoxy-5-(tetrahydro-pyran-2-yl-methoxy)-2H-phthalazin-1-one

A solution of 5-hydroxy-6-methoxy-2H-phthalazin-1-one (1.5 g, 7.81 mmoles), obtained as described in example 18, in dimethylformamide (40 ml) was added with Na$_2$CO$_3$ (1.65 g, 15.61 mmoles) and KI in catalytic amount and the mixture was heated to 90° C. in nitrogen atmosphere. A solution of methansulfonic acid tetrahydropyran-2-ylmethyl ester (6.1 g, 31.46 mmoles), obtained as described in example 41, in dimethylformamide (14 ml) was dropped therein. After 24 hours the mixture was poured into water and thrice extracted in ethyl acetate. The organic phases were washed with water till neutrality then anhydrified and concentrated under vacuum to give a solid which tritured in ethyl ether yielded 1.66 g of the title product (yield: 66%)

EXAMPLE 43

Synthesis of 1-Chloro-6-methoxy-5-(tetrahydro-pyran-2-yl-methoxy)-phthalazine

Operating analogously to example 7 staring from 6-methoxy-5-(tetrahydropyran-2-yl-methoxy)-2H-phthalazin-1-one (1.48 g, 5.12 mmoles), obtained as described in example 42, and phosphoryl chloride (6 ml) 1.65 g of the title product as a crude were obtained and used as such in the next step.

EXAMPLE 44

Synthesis of 1(3,5-Dichloropyridin-4-yl-methoxy-5-(tetrahydro-pyran-2-yl-methoxy)-phthalazine (Compound 11)

Operating analogously to example 8 using 1-chloro-6-methoxy-5-(tetrahydropyran-2-yl-methoxy-phthalazine, obtained as described in example 43, in dimethylformamide, 55% NaH and 3,5-dichloro-4-methyl-pyridine in dimethylformamide, the title product was obtained (yield: 35%).

$^1$H-NMR (300 MHz, CDCl$_3$) δ (ppm): 9.77 (s, 1H); 8.50 (s, 2H); 7.91 (d, 1H, JHH=9.0 Hz); 7.62 (d, 1H); 4.86 (s, 2H); 4.18–4.05 (m, 2H); 4.06–3.42 (m, 3H); 4.04 (s, 3H); 1.94–1.38 (m, 6H).

EXAMPLE 45

Synthesis of 1-(3,5-Dichloropyridin-4-yl-methyl)-6-methoxy-5-(tetrahydro-pyran-2-yl-methoxy)-phthalazin-3-oxide (Compound 12)

Operating analogously to example 9 starting from 1-(3,5-dichloropyridin-4-ylmethyl)-6-methoxy-5-(tetrahydropyran-2-yl-methoxy)-phthalazine (0.2 g, 0.48 mmoles) obtained as described in example 44, in methylene chloride (2 ml) and m-chloroperbenzoic acid (0.143 g, 0.58 mmoles) 0.104 g of the tide product was obtained (yield: 48%).

$^1$H-NMR (200 MHz, CDCl$_3$) δ (ppm): 8.82 (s, 1H); 8.50 (s, 2H); 7.84 (d, 1H, JHH=9.0 Hz); 7.39 (d, 1H); 4.78 (s, 2H); 4.13–3.98 (m, 3H); 4.02 (s, 3H); 3.74–3.41 (m, 2H); 1.91–1.35 (m, 6H).

EXAMPLE 46

Synthesis of Methansulfonic Acid Tetrahydro-furan-3-yl Ester

A solution of tetrahydrofuran-3-ol (4.6 g, 52.2 moles) in methylene chloride (70 ml) at 0° C. was added with triethylamine (8.36 ml, 60 moles) and mesyl chloride (4.44 ml, 57.4 moles) in methylene chloride (85 ml). The temperature was left to rise to room value and after 1 hour the mixture was poured into water and in methylene chloride. The organic phases were anhydrified and dried to give 8.12 g of the title product (yield: 93%).

EXAMPLE 47

Synthesis of 6-Methoxy-5-tetrahydro-furan-3-yloxy)-2H-phthalazin-1-one

Operating analogously to example 42 using 5-hydroxy-6-methoxy-2H-phthalazin-1-one (1.55 g, 8.07 mmoles) obtained as described in example 18, in dimethylformamide (35 ml), sodium carbonate (1.71 g, 16.13 mmoles), potassium iodide in catalytic amount and methansulfonic acid tetrahydrofuran-3-yl ester (2.01 g, 12.1 mmoles) obtained as described in example 46, in dimethylformamide (10 ml), 0.73 g of the tide product was obtained (yield: 86%).

EXAMPLE 48

Synthesis of 1-Chloro-6-methoxy-5-(tetrahydro-furan-3-yloxy)-phthalazine

Operating analogously to example 7 starting from 6-methoxy-5-(tetrahydro-furan-3-yloxy)-2H-phthalazin-1-one (1.73 g, 6.6 mmoles) and phosphoryl chloride (6.7 ml, 73 mmoles), 1.63 g of the title product were obtained (yield: 88%).

EXAMPLE 49

Synthesis of 1-(3,5-Dichloropyridin)-4-ylmethy)-6-methoxy-5-(tetrahydrofuran-3-yloxy)-phthalazine (Compound 13)

Operating analogously to example 8 starting from 3,5-dichloro-4-methyl-pyridine (2.47 g, 16.89 mmoles), sodium hydride (0.74 g, 16.89 mmoles), 1-chloro-6-methoxy-5-(tetrahydrofuran-3-yloxy)-phthalazine (1.58 g, 5.63 mmoles) obtained as described in example 48, in dimethylformamide (35 ml) 0.74 g of the title product (yield: 63%) were obtained.

$^1$H-NMR (300 MHz, CDCl$_3$) δ (ppm): 9.65 (s, 1H); 8.49 (s, 2H); 7.93 and 7.65 (2d, 2H, JHH=9.0 Hz); 5.36–5.28 (m, 1H); 4.86 (s, 2H); 4.22–3.80 (m, 4H); 4.05 (s, 3H); 2.32–2.00 (m, 4H).

EXAMPLE 50

Synthesis of 1-(3,5-Dichloropyridin-4-ylmethyl)-6-methoxy-5-tetrahydrofuran-3-yloxy)-phthalazin-3-oxide and 1-(3,5-Dichloro-1-oxy-pyridin-4-ylmethyl)-6-methoxy-5-(tetrahydrofuran-2-yloxy)-phthalazine 3-Oxide (Compound 14 and 19)
Operating analogously to example 9 starting from 1-(3,5-dichloropyridin-4-ylmethyl)-methoxy-5-(tetrahydrofuran-3-yloxy)-phthalazine (0.74 g, 1.82 mmoles) obtained as described in example 49, in methylene chloride (4 ml) and m-chloroperbenzoic acid (0.72 g, 2.93 mmoles), 0.331 g of the first title product was obtained. From the chromatographic column 0.207 g of the second title product was eluted (eluent:methylene chloride/methanol 9:1)

First product: $^1$H-NMR (200 MHz, CDCl$_3$) δ (ppm): 8.67 (s, 1H); 8.50 (s, 2H); 7.86 and 7.41 (2d, 2H, JHH=8.9 Hz); 5.30–5.24 (m, 1H); 4.80 (s, 2H); 4.15–3.76 (m, 4H); 4.04 (s, 3H); 2.26–2.00 (m, 4H).

Second product: $^1$H-NMR (200 MHz, CDCl$_3$) δ (ppm): 8.68 (s, 1H); 8.19 (s, 2H); 7.85 (d, 1H, JHH=9.1 Hz); 7.42 (d, 1H); 5.32–5.25 (m, 1H); 4.73 (s, 2H); 4.05 (s, 3H); 4.16–3.76 (m, 4H); 2.20–2.00 (m, 2H.

EXAMPLE 51

Synthesis of 6-Hydroxy-5-(tetrahydrofuran-2-yloxy)-2H-phthalazin-1-one

A solution of 6-methoxy-5-(tetrahydrofuran-2-yloxy)-2H-phthalazin-1-one (680 mg, 2.6 mmoles), obtained as described in example 47, in DMF (15 ml) and sodium p-thiochresolate (378.6 mg, 2.6 mmoles) was heated to 90° C. for 10 hours, poured into water, acidified at pH 6–7 with 1M HCl, dried, take up in water and dried again. The crude was chromatographed (eluent:methylene chloride/methanol 9:1) to give 330 mg of the title product (yield: 52%).

$^1$H-NMR (200MH, DMSO) δ (ppm): 12.41 (s, 1H); 11.07 (s-broad, 1H); 8.23 (s, 1H); 7.82 (d, 1H, JHH=8.8 Hz); 7.44 (d, 1H); 5.25–5.20 (m, 1H); 4.03–3.59 (m, 4H); 2.11–2.00 (m, 2H)

EXAMPLE 52

Synthesis of 6-Difluoromethoxy-5-(tetrahydro-furan-2-yloxy)-2H-phthalazin-1-one

6-Hydroxy-5-(tetrahydrofuran-2-yloxy)-2H-phthalazin-1-one (320 mg, 1.29 mmoles), obtained as described in example 51, in dry DMF (80 ml) and K$_2$CO$_3$ (267 mg, 1.93 mmoles) were treated with Freon-22 (5 g, 58 mmoles) at 0.5 bar. The mixture was brought to 115° C. for 1 night, then dried and chromatographed (eluent:benzene/ethyl acetate 1:1, then ethyl acetate only) to give 300 mg of the title product (yield: 78%).

$^1$H-NMR (200 MHz, CDCl$_3$) δ (ppm): 10.62 (s, 1H); 8.44 (s, 1H); 8.16 (d, 1H, JHH=9.2 Hz); 7.55 (d, 1H); 6.63 (t, 1H, 3H=72 Hz); 5.24–5.18 (m, 1H); 4.18–3.75 (m, 4H); 2.29–2.09 (m, 2H).

EXAMPLE 53

Synthesis of 1-Chloro-6-difluoromethoxy-5-(tetrahydro-furan-2-yloxy)-phthalazine A solution of 6-difluoromethoxy-5-(tetrahydrofuran-2-yloxy)-2H-phthalazin-1-one (280 mg, 0.94 mmoles), obtained as described in example 52, and POCl$_3$ (1.2 ml) was heated to 90° C. for 1.5 hours, then dried, taken up in methylene chloride, washed with a saturated solution of NaHCO$_3$, then twice with water, anhydrified and dried to give 296 g of the title product (yield: 99.7%).

EXAMPLE 54

Synthesis of 1-(3,5-Dichloro-pyridin-4-ylmethyl)-6-difluoromethoxy-5-(tetrahydro-furan-3-yloxy)-phthalazine (Compound 15)

A solution under nitrogen of 3,5-dichloro-4-methyl-pyridine (457 mg, 2.82 mmoles) in dry DMF (10 ml) was portionwise added with 60% NaH (113 mg, 2.82 mmoles) and, after 1 hour at room temperature, was dropwise added, at a temperature <10° C., with 1-chloro-6-difluoromethoxy-5-(tetrahydrofuran-2-yloxy)-phthalazine (296 mg, 0.937 mmoles), obtained as described in example 53, in dry DMF (10 ml). After 2 hours at room temperature the mixture was poured into a 0.4M buffer at pH=7 (50 ml), extracted in ethyl acetate (2×50 ml) and the organic phase was washed with water, anhydrified and concentrated under vacuum. The residue was chromatographed (eluent:benzene/ethyl acetate 1:1, then ethyl acetate only), then crystallized from ethyl ether/benzene to give 180 mg of the title product (yield: 43.5%).

$^1$H-NMR (200 MHz, CDCl$_3$) δ (ppm): 9.72 (s, 2H); 8.52 (s, 2H); 7.96 (d, 1H, JHH=9.2 Hz); 7.80 (d, 1H); 6.68 (t, 1H, JHF=74 Hz); 5.34–5.29 (m, 1H); 4.91 (s, 2H); 4.22–3.81 (m, 4H); 2H).

EXAMPLE 55

Synthesis of 1-(3,5-Dichloro-pyridin-4-ylmethy-6-difluoromethoxy-5-(tetrahydro-furan-3-yl-oxy)-phthalazine 3-oxide and 1-(3,5-dichloro-1-oxy-pyridin-4-ylmethyl)-6-difluoromethoxy-5-tetrahydro-furan-3-yloxy)-phthalazine 3-oxide (Compound 16 and 17)

A solution of 1(3,5-dichloro-pyridin-4-ylmethyl)-6-difluoromethoxy-5-(tetrahydro-furan-3-yloxy)-phthalazine (1.5 g, 3.39 mmoles) in methylene chloride (20 ml) and 55% m-chloroperbenzoic acid (1.56 g, 4.99 mmoles) was kept under nitrogen for 2 hours at room temperature.

The mixture was evaporated to dryness, taken up in water, neutralized with NaHCO$_3$, extracted in ethyl acetate, anhydrified and dried. The crude oil was chromatographed (eluent:ethyl acetate, then ethyl acetate/methanol 7:3), then tritured in petrolatum/ethyl ether 8:2, filtered, washed with petrolatum and dried under vacuum to give 0.5 g of the first title product (yield: 32.25%) and 0.6 g of the second title product (yield: 37.33%).

First product: $^1$H-NMR (200 MHz, CDCl$_3$) δ (ppm): 8.67 (m, 1H); 8.47 s, 2H); 7.86 (d, 1H, JHH=9.2 Hz); 7.53 (d, 1H); 6.69 (t, 1H, JHF=72 Hz); 5.29–5.23 (m, 1H); 4.80§, 2H); 4.13–3.75 (m, 4H); 2.23–2.11 (m, 2H).

Second product: $^1$H-NMR (200 MHz, CDCl$_3$) δ (ppm): 8.68 (m, 1H); 8.19§, 2H); 7.84 (d, 1H, JHH=9.2 Hz); 7.54 (d, 1H); 6.68 (t, 1H, JHF=72 Hz); 5.30–5.25 (m, 1H); 4.75§, 2H); 4.15–3.76 (m, 4H); 2.24–2.16 (m, 2H).

EXAMPLE 56

Synthesis of [1,4-bis(Diphenylphosphino(butane]-dichloropalladium(II)

A solution of PdCl$_2$(CH$_3$CN)$_2$ (405 mg, 1.561 mmoles) in benzene under nitrogen and magnetic stirring was added with 1,4-diphenylphosphanyl)butane (665 mg, 1.561 mmoles). After 1.5 hours a precipitate formed and was added with hexane (10 ml), filtered, washed with hexane and dried under vacuum to give 620 mg of the tide product (66%).

EXAMPLE 57

Synthesis of 6-Methoxy-1-phenyl-5-tetrahydro-furan-2-yloxy)-phthalazine (Compound 18)

A suspension of magnesium (0.078 g, 3.21 mmoles) in tetrahydrofuran (1 ml) was dropwise added, under nitrogen and stirring with a solution of 1,2-dibromoethane (0.3 g, 1.6 mmoles), 3-bromo-pyridine (0.25 g, 1.6 mmoles) in tetrahydrofuran (1 ml). 30 Minutes after the end of the dropping a solution of ZnCl$_2$ (0.22 g, 1.6 mmoles) in tetrahydrofuran (3 ml) was added. After 20 minutes [1,4-bis (diphenylphosphino(butane]-dichloropalladium(II) (0.016 g, 0.026 mmole), obtained as described in example 57, and 1-chloro-6-methoxy-5-(tetrahydro-furan-3-yloxy)-phthalazine (0.15 g, 0.53 mmole) obtained as described in example 48, were added and the mixture was refluxed for 1.5 hours, then cooled, washed with water and extracted in ethyl acetate. The organic phase was anhydrified and dried. The aqueous phase was evaporated and taken up in ethyl acetate. The joined organic phases were dried and the residue flash chromatographed (eluent:methylene chloride/methanol 9:1) to give 0.071 g of the title product.

$^1$H-NMR (200 MHz, CDCl$_3$) δ (ppm): 9.79 (s, 1H); 8.96–7.35 (m, 4H); 7.77–7.54 (m, 2H); 5.37–5.32 (m, 1H); 4.24–3.80 (m, 6H); 4.02 (s, 3H); 2.34–2.01 (m, 2H).

EXAMPLE 58

Synthesis of 5,6-Dimethoxy-3H-isobenzofuran-1-one

Under mechanical stirring a slurry of 3,4-dimethoxybenzoic acid (353.5 g, 1.94 moles) in HCHO (1.71, 24.5 moles) was prepared and cooled in ice, saturated with gaseous HCl (340 g, 9.32 moles), then gradually brought to 60° C. After 1 night the temperature was brought to room value and further HCl (300 g) was gurgled therein, then the temperature was brought to 60° C. again overnight. The mixture was brought to small volume, taken up in water (1 l), neutralized with 28% NH$_4$OH (1.5 l) and kept at cold for 2 hours, then filtered. The filtrate was washed with water till neutrality, then crystallized from methanol (2 l) and dried under vacuum at 60° C. to give 220 g of the title product (yield: 58.65%).

$^1$H-NMR (200 MHz, CDCl$_3$) δ (ppm): 7.28 and 6.28 (2s, 2H); 5.20 (s, 2H); 3.95 and 3.91 (2s, 6H).

EXAMPLE 59

Synthesis of 2-Formyl-4,5-dimethoxy-benzoic Acid

A mixture under nitrogen of 5,6-dimethoxy-3H-isobenzofuran-1-one (10 g, 51.5 mmoles), obtained as described in example 58, in carbon tetrachloride (250 ml), N-bromo-succinimide (13.88 g, 77.25 mmoles) and benzoyl peroxide (320 mg, 1.23 mmoles) was refluxed for 2 hours, then cooled, filtered and washed with a solution of 10% Na$_2$SO$_3$ (200 ml), then with water, anhydrified and dried. The residue was taken up in 5% HCl (100 ml) and refluxed for 4 hours, then the solution was cooled, alkalinized with NaOH, washed with ethyl acetate and slowly acidified to give a precipitate which was filtered, washed with water and dried over P$_2$O$_5$ under vacuum to give 6.43 g of the title product (yield: 60%).

EXAMPLE 60

Synthesis of 5,6-Dimethoxy-3-(triphenyl-$\lambda^6$-phosphanyl)-3H-isobenzofuran-1-one A slurry under nitrogen of 2-formyl-4,5dimethoxy-benzoic acid (6.43 g, 30.62 mmoles), obtained as described in example 59, triphenyl-phosphine (8.3 g, 30.62 mmoles), HBr in 30% acetic acid (8.26 ml, 30.62 mmoles) and glacial acetic acid (20 ml) was heated to 90° C. for 4.5 hours. The mixture was dried, dissolved in acetonitrile (50 ml) and diluted with ethyl ether till slurry, then cooled and filtered, and the filtrate was washed with ethyl ether and dried under vacuum to give 13.6 g of the title product (yield: 83%).

$^1$H-NMR (200 MHz, DMSO) δ (ppm): 8.35 and 7.31 (2s, 2H); 8.03–7.66 (m, 15H); 6.01 (s, 1H); 3.84 and 3.45 (2s, 6H).

EXAMPLE 61

Synthesis of 5,6-Dimethoxy-3-pyridin-4-ylmethylen-3H-isobenzofuran-1-one

In a slurry of 5,6-dimethoxy-3-triphenyl-$\lambda^6$-phosphanyl)-3H-isobenzofuran-1-one (78 g, 145 mmoles), obtained as described in example 60, and 4-pyridincarboxaldehyde (13 ml, 145 mmoles) in methylene chloride (1 l), triethylamine (20 ml, 145 mmoles) was dropped at room temperature under stirring. After 1.5 hours the mixture was filtered and dried and the residue treated with ethanol at reflux, cooled and filtered. The mother liquor was chromatographed (eluent:methylene chloride then with 1% of methanol) and the residue dried and joined with the filtrate above to give 25 g of the title product.

EXAMPLE 62

Synthesis of 6,7-Dimethoxy-4-pyridin-4-ilmethyl-2H-phthalazin-1-one 5,6-Dimethoxy-3-pyridin-4-ylmethylen-3H-isobenzofuran-1-one (25 g, 88.34 mmoles), obtained as described in example 61, was reacted with hydrate hydrazine (500 ml) for 2 hours at room temperature under stirring, then for 1 hour at reflux. The mixture was diluted with water (300 ml), cooled and filtered to give 23 g of the tide product (yield: 87%).

EXAMPLE 63

Synthesis of 1-Chloro-6,7-dimethoxy-4-pyridin-4-ylmethyl-phthalazine

A slurry of 6,7-dimethoxy-4-pyridin-4-ylmethyl-2H-phthalazin-1-one (10 g, 33.6 mmoles), obtained as described in example 62, in $POCl_3$ (70 ml) was heated to 90° C. for 4 hours. $POCl_3$ was evaporated and the residue dissolved in water, a saturated solution of $NaHCO_3$ and NaOH till the formation of a precipitate which was filtered and suspended in methanol, dried, suspended in acetone and filtered again. The residue was dried at 45° C. under vacuum to give 9.56 g of the title product.

EXAMPLE 64

Synthesis of 1-Benzyl-6,7-dimethoxy-4-pyridin-4-ylmethyl-phthalazine (Compound 20)

In anhydrous environment, $ZnCl_2$ (863 mg, 6.33 mmoles) was dissolved in tetrahydrofuran (20 ml), and a 2M solution of benzyl magnesium chloride in tetrahydrofuran (3.2 ml, 2.5 equivalents) was dropped therein. After 30 minutes 1-chloro-6,7-dimethoxy-4-pyridin-4-ylmethyl-phthalazine (800 mg, 2.53 mmoles), obtained as described in example 63, palladium acetate (71 mg, 0.316 mmole) and triphenylphosphine (166 mg, 0.633 mmole) were added and the whole was refluxed. After 1 hour the mixture was poured into a saturated solution of $NH_4Cl$ and by adding ethyl acetate a solid precipitated. The whole was evaporated to dryness and the residue taken up in methylene chloride and extracted with concentrated ammonia. The organic phase was dried to yield a residue which was chromatographed (eluent:methylene chloride/2% methanol, then methylene chloride/5% methanol). The oily eluate was dissolved in methylene chloride and by adding HCl/ethyl ether a precipitate formed which was tritured in ethyl acetate and filtered to give 788 mg of the title product (yield: 64.8%).

$^1$H-NMR (200 MHz, DMSO) δ (ppm): 8.89–8.06 (m, 4H); 7.96 and 7.86 (2, 2H); 7.54–7.19 (m, 5H); 5.23 and 5.04 (2s, 4H); 4.08 and 4.03 (2s, 6H).

EXAMPLE 65

Synthesis of 1-Bromo-6,7-dimethoxy-4-pyridin-4-ylmethyl-phthalazine 6,7-Dimethoxy-4-pyridin-4-ylmethyl-2H-phthalazin-1-one (5 g, 16.8 mmoles), obtained as described in example 62, was suspended in acetonitrile (30 ml) and added with $POBr_3$ (14.5 g, 50.4 mmoles). More acetonitrile was added (total 65 ml) and the mixture was heated to 70° C. for 16 hours. More $POBr_3$ (8.1 g) was added and the heating kept on for 7 hours. The solid was filtered off and the mother liquor poured into 1N KOH and extracted with ethyl acetate. The filtrate was slowly put in KOH and extracted with $CH_2Cl_2$. The organic extracts were joined, anhydrified over $Na_2SO_4$ and the solvent evaporated. The residue was crystallized from $CH_2Cl_2$, and the mother liquor was dissolved in methylene chloride/1% methanol and chromatographed (eluent:methylene chloride/2% methanol then methylene chloride/3% methanol). Joining the crystallized and the eluate 1.89 g of the title product were obtained (yield: 31%).

EXAMPLE 66

Synthesis of 6,7-Dimethoxy-1-phenyl-4-pyridin-4-ylmethyl-phthalazine (Compound 21)

In dry environment, $ZnCl_2$ (379 mg, 2.78 mmoles) was dissolved in tetrahydrofuran (20 ml), then the temperature was brought to 0° C. and a 2M solution of phenyl lithium in hexane (1.4 ml, 2.8 mmoles) was dropped therein. The temperature was left to rise to room value and 1-bromo-6,7-dimethoxy-4-pyridin-4-ylmethyl-phthalazine (500 mg, 1.39 mmoles), obtained as described in example 65, palladium acetate (15 mg, 0.0695 mmole) and triphenylphosphine (36 mg, 0.139 mmole) were added and the whole was refluxed for 1.5 hour. The reaction was stopped with some drops of NaOH, then the mixture was dried and the residue taken up in water and $CH_2Cl_2$. The organic phase was dried to yield a residue which was chromatographed (eluent:methylene chloride, then methylene chloride/2% methanol, then methylene chloride/5% methanol). The eluate was dissolved in methylene chloride, treated with TONSIL® and filtered over celite. The mother liquor was dried yielding 172 mg of the title product.

$^1$H-NMR (200 MHz, DMSO) δ (ppm): 8.83–7.96 (m, 4H) 7.85–7.64 (m, 5H); 7.82 (s, 1H); 7.37 (s, 1H); 5.00 (s, 2H); 4.07 and 3.89 (2s, 6H).

EXAMPLE 67

PDE 4 Enzyme Inhibition Test a) Purification of Human Polymorphonucleate Leukocytes The polymorphonucleate leukocytes (PMNs) were isolated from peripheral blood of healthy volunteers according to what described by Boyum A, Scand. J. Immunol., 1976, 5° suppl., 9). Shortly, the isolation of the PMNs was effected by Ficoll-Paque gradient centrifugation followed by sedimentation on dextrane and the erythrocyte contamination was eliminated by hypotonic lysis.

b) PDE 4 Enzyme Purification

The human PMNs were resuspended in TRIS/HCl buffer (10 mM pH 7.8) containing $MgCl_2$ (5mM), EGTA (4 mM), mercaptoethanol (5 mM), TRITON-X100 (1%), pepstatin A (1 μM), PMSF (100 μM) and leupeptin (1 μM), and homogenised by Polytron. The homogenate was centrifuged at 25,000×g for 30 minutes at 4° C. and the surnatant was used for the PDE 4 enzyme purification by ion exchange chromatography using the FPLC technique according to what described by Schudt C. et al., Naunyn-Schmidberg's Arch. Pharmacol., 1991, 334, 682. The surnatant was seeded on a UNO Q12 column (Bio-Rad) and the enzyme was eluted by sodium acetate gradient from 50mM to 1M. The fractions containing enzymatic activity were joined, dialysed against water and concentrated. The resulting PDE 4 enzyme was stored at −20° C. in the presence of ethylenglycole (30%) v/v) until use.

c) PDE 4 Enzyme Inhibition

The enzyme activity was assessed with an Amersham kit based on the SPA technique (Scintillation Proximity Assay). The enzymatic reaction was effected in a total volume of 100 µl of TRIS/HCl buffer (50 mM, pH7.5), $MgCl_2$ (8.3mM), EGTA (1.7 mM), cAMP (1µM) and [$^3$H]cAMP (~100.000 dpm). The compounds of the invention and the reference ones were added at the wanted concentrations. As reference compounds 6,7 dimethoxy-4-(pyridin-4-ylmethyl)-2H-phthalazin-1 on (reference 1) and 6,7-dimethoxy-4-(piperidin-4-ylmethyl)-2H-phthalazin-1-one (reference 2) embraced by the general formula of the patent application EP-0 722 936 (in the name of Eisai) were used. The reaction was started by adding the enzyme (15 µg protein/ml) in 40 minutes at 30° C. and stopped with 50 µl of SPA particles suspension. The radioactivity of the particles was measured in β-emitting counter. The $IC_{50}$ values were computed over 9 equidistant concentrations in logarithmic scale using a 4-parameters logistic function by a software. The results are set forth in Table 1.

TABLE 1

| Compound | PDE 4% inhibition (M) | | | $IC_{50}$ nM |
| --- | --- | --- | --- | --- |
|  | $10^{-5}$ | $10^{-6}$ | $10^{-8}$ |  |
| 1 |  | 84 | 19 | 53.1 ± 10 |
| 2 | 97 | 94 | 25 | 42.4 ± 5 |
| 3 |  | 100 | 34 | 38.9 ± 7 |
| 4 |  | 73 |  | 58.9 ± 5 |
| 5 |  | 80 | 33 | 29.5 ± 4 |
| 6 |  | 79 | 27 | 56.8 ± 9 |
| 7 |  |  |  | 186 ± 43 |
| 9 |  |  |  | 146 ± 38 |
| 10 | 93 | 80 | 33 | 74.9 ± 8 |
| 13 |  |  |  | 153 ± 85 |
| 14 |  |  |  | 298 ± 37 |
| 15 |  |  |  | 282 ± 36 |
| 19 |  |  |  | 206 ± 124 |
| Reference 1 |  |  |  | >100 µM |
| Reference 2 |  |  |  | >100 µM |

EXAMPLE 68

$TNF_{60}$ Inhibition Test a) Human Monocytes Isolation

The monocytes were isolated from peripheral blood of healthy volunteers according the procedure of Schreek L., J. Natl. Cancer Inst., 1964, 32, 507. The monocytes and lymphocytes population was isolated by Ficoll gradient centrifugation, and the cells diluted at a density of $2.5 \times 10^6$ cells/ml in RPMI1640 incubation containing 1% inactivated bovine fetal serum, penicillin (100 U/ml) and streptomycin (100 U/ml) were placed in 24-wells plates (1 ml/well) and left to adhere for 1 hour at 37° C. with 5% $CO_2$. At the end of the incubation the lymphocytes not adhering were removed by aspiration and the monocytes adhered to the plate were used in the next step.

b) $TNF_\alpha$ Synthesis Inhibition

The $TNF_\alpha$ synthesis from human monocytes was measured according to the method of Barnette M. et al., Biochemical Pharmacology, 1996, 51, 949. The monocles were incubated for 1 hour with 1 ml of RPMI1640 incubation medium (1% inactivated bovine serum, 100 U/ml penicillin and streptomycin) containing different concentrations of the products according to the present invention or the carrier only for the controls. The $TNF_\alpha$ synthesis from monocytes was induced by adding 1ng/ml of LPS (lipopolysaccharide of E. Coli) and after 16 hours of incubation at 37° C., 5% $CO_2$, the incubation medium was removed, and the surnatant stored at −80° C. until the measurement. The $TNF_\alpha$ levels were determined by ELISA test with an Amersham kit. The results are set forth in Table 2 as $IC_{50}$ measured with the same calculation of example 67.

TABLE 2

| Compound | $IC_{50}$ nM |
| --- | --- |
| 1 | 254 ± 84 |
| 2 | 139 ± 55 |
| 3 | 167 ± 79 |
| 4 | 187 ± 35 |
| 5 | 252 ± 120 |
| 6 | 83.5 ± 24 |
| 10 | 259 ± 86 |
| 14 | 389 ± 47 |

EXAMPLE 69

PDE 3 and 5 Enzymes Inhibition Test a) Human Platelet Preparation

Human platelets were prepared from platelet rich plasma (PRP) obtained from the Hematological Dept. of the "L.Sacco" Hospital of Milan. The PRP was centrifuged at 2,200 rpm for 15 minutes at 4° C. and the pellet was suspended in lysis solution (15 ml; 155 mM $NH_4Cl$, 10 mM $KHCO_3$ and 0.1 mM $Na_2EDTA$, pH=7.4) and incubated for 10 minutes on ice-bath to remove the erythrocyte contamination. After a centrifuging at 1,400 rpm for 10 minutes at 4° C., platelets were suspended in 10 ml of 145 nM NaCl, 5 mM KCl, 1 mM $MgSO_4$, 10 mM glucose, 10 mM HEPES and 0.05 U/ml of hirudin (pH=7.4), and stored at −20° C. until homogenization and chromatography.

b) Purification of PDE 3 and PDE 5 with Fast Protein Liquid Chromatography (FPLC)

Before the chromatographic step, platelets were thawed and 50 ml of 20 mM TRIS (pH=6.5) containing 5 mM βmercapto-ethanol, 2 mM EDTA, 50mM sodium acetate and 50 µM PMSF (homogenization buffer) were added. The platelet suspension was then homogenized by a Polytron homogenizer (Polytron PT 1200) for 20 seconds. The homogenate was centrifuged at 14,500 rpm for 20 minutes at 4° C., and the supernatant was applied to a UNO Q12 column (Bio-Rad) pre-equilibrated with the PMSF. A flow rate of 4.5 ml/min was used throughout the ion exchange chromatography procedure. The column was washed with PMSF (180 ml) and PDE 3 and PDE 5 were eluted by sodium acetate linear gradient from 0.05M to 1M. The fractions containing enzymatic activity were joined, dialysed against water and concentrated 10 times by ultrafiltration. The resulting solution was stored at −20° C. in the presence of ethylenglycole (30%) v/v) until use.

c) Assay of Phosphodiesterase Activity

The enzyme activity was assessed with an Amersham kit based on the SPA technique (Scintillation Proximity Assay). The enzymatic reaction was effected in a total volume of 100 µl of TRIS/HCl buffer (50 mM, pH7.5), $MgCl_2$ (8.3 mM), EGTA (1.7 mM), cAMP (for PDE 3 assay) or cGMP (for PDE 5 assay) (1 µM), [$^3$H]cAMP or [$^3$H]cGMP (10 µl), and and 10 µl of the compounds of the invention. The reaction was started by adding the enzyme (10 µl) incubated for 40 minutes at 30° C. and stopped by adding 50 µl of SPA beads. The radioactivity due to the particles was measured in β-emitting counter. The results are expressed as percent activity versus the control present in each test.

TABLE 3

| Compound | PDE 3<br>% inhibition<br>at $10^{-6}$ M | PDE 5<br>% inhibition<br>at $10^{-6}$ M |
| --- | --- | --- |
| 1 | 0 | 20 |
| 2 | 20 | 4 |
| 3 | 5 | 14 |
| 4 | 8 | 19 |
| 6 | 25 | 20 |
| 10 | 20 | 20 |
| 13 | 4 | 2 |
| 15 | 11 | 0 |
| 19 | — | 8 |

What is claimed is:

1. A compound of formula I

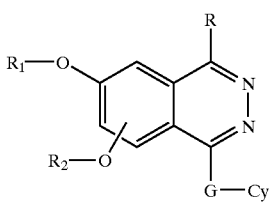
(I)

wherein G is methylene, ethylene, imino, CONH or a bond;

Cy is phenyl or a 5- or 6-membered heterocycle of the group consisting of pyrrole, imidazole, pyrazole, pyrrolidine, pyrroline, imidazoline, imidazolidine, pyrazolidine, pyrazoline, pyridine, pyrazine, pyrimidine, pyridazine, piperazine, piperidine, and triazine, the Cy residue being optionally substituted by one or more substituent(s) selected from the group consisting of keto, nitro, carboxy, fluorine, chlorine, bromine, or iodine;

R is H, phenyl or a $(C_{1-4})$alkyl group optionally substituted by phenyl;

$R_1$ is a $(C_{1-6})$alkyl or polyfluoro$(C_{1-6})$alkyl group;

$R_2$ is aryl, aryl-$(C_{1-10})$-alkyl, $(C_{4-7})$cycloalkyl or $(C_{4-7})$ heterocycle wherein the heteroatom is an oxygen atom; and the derivatives of formula (I) in which one and/or the other of the nitrogens of the phthalazine central nucleus as well as the nitrogens on the substituent Cy may be an N→O oxide, or the pharmaceutically acceptable salts thereof;

with the proviso that when R is H, $R_2$ is not aryl-methyl.

2. A compound according to claim 1 wherein G is methylene or imino; Cy is phenyl or a 5- or 6-membered heterocycle containing from 1 to 3 nitrogen atom(s), being both the residues substituted by one or two halogen(s); R is H, phenyl or a $(C_{1-4})$alkyl group optionally substituted by phenyl; $R_1$ is a $(C_{1-4})$alkyl or polyfluoro$(C_{1-6})$alkyl group; $R_2$ is a $(C_{4-7})$cycloalkyl or $(C_{4-7})$heterocycle wherein the heteroatom is an oxygen atom; and derivatives of formula (I) in which one and/or the other of the nitrogens of the phthalazine central nucleus may be an N→O oxide, or the pharmaceutically acceptable salts thereof.

3. A compound according to claim 1 wherein G is methylene; Cy is phenyl or a 6-membered heterocycle containing 1 nitrogen atom, being both the residues substituted by one or two halogen(s); R is phenyl or a $(C_{1-4})$alkyl group optionally substituted by phenyl; $R_1$ is a $(C_{1-6})$alkyl or polyfluoro$(C_{1-6})$alkyl group; $R_2$ is a $(C_{4-7})$cycloalkyl or $(C_{4-7})$heterocycle wherein the heteroatom is an oxygen atom; and derivatives of formula (I) in which one and/or the other of the nitrogens of the phthalazine central nucleus may be an N→O oxide, or the pharmaceutically acceptable salts thereof.

4. A process for preparing a compound according to claim 1 wherein G is methylene, ethylene, imino or a bond, characterized in that a benzaldehyde of formula II

(II)

wherein $R_1$ and $R_2$ are as defined in claim 1 is oxidised to give an acid of formula III

(III)

wherein $R_1$ and $R_2$ are as defined above, which is transformed into the corresponding acyl halide of formula IV

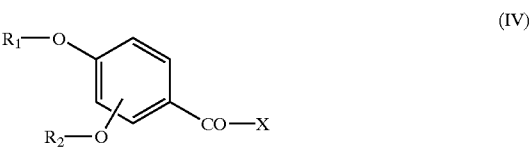
(IV)

wherein $R_1$ and $R_2$ are as defined above and X is chlorine or bromine: this compound is reacted with diethylamine to give a benzamide of formula V

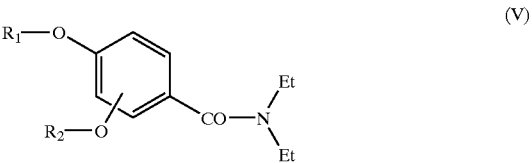
(V)

wherein $R_1$ and $R_2$ are as defined above, which reacted with dimethylformamide in the presence of a strong base yields a compound of formula VIa

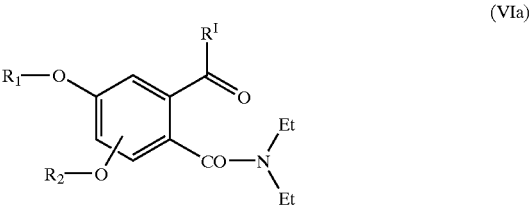
(VIa)

wherein $R_1$ and $R_2$ are as defined above, and $R^I$ is hydrogen, which, when a compound of formula I wherein R is hydro gen is desired, is reacted with tert-butylcarbazole to give the compound of formula VIIa

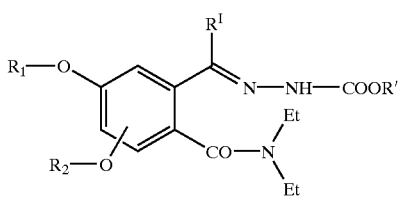

(VIIa)

wherein $R^1$, $R_1$ and $R_2$ are as defined above, and R' is a protecting group of the carboxy moiety; instead when a compound of formula I wherein R is other than hydrogen is desired, the compound of formula VIa is treated with a $R''$-magnesium halide or $R''$-lithium, wherein $R''$ is phenyl or a $(C_{1-4})$alkyl group optionally substituted by an aromatic or hydrogenated ring having from 5 to 7 members, to give a compound of formula XIII

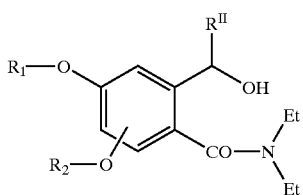

(XIII)

wherein $R''$, $R_1$ and $R_2$ are as defined above, which treated with a suitable oxidising agent, yields a compound of formula VIb

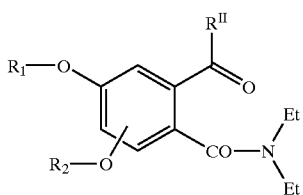

(VIb)

wherein $R_1$, $R_2$ and $R''$ are as defined above, which is treated with tert-butylcarbazole to give the compound of formula VIIb, differing from the compound VIIa in that R has the meanings of formula I hydrogen excluded; the compound of formula VIIa or VIIb is reacted with triffuoroacetic acid to give the phthalazinone of formula VIII

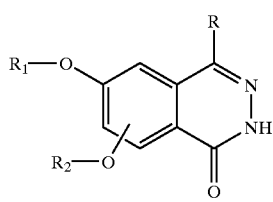

(VIII)

wherein R, $R_1$ and $R_2$ are as defined above; this is reacted with a halogenating agent to give the phthalazine of formula IX

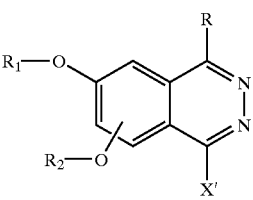

(IX)

wherein R, $R_1$ and $R_2$ are as defined above, and X' is a halogen atom, which by treatment with a compound of formula XIV Cy-G'Y  (XIV)

wherein Cy is as defined in claim 1, G' is methylene, ethylene, amino or a bond and Y is hydrogen or halogen, provides the desired compound.

5. A pharmaceutical composition containing a therapeutically amount of a compound according to claim 1 in admixture with a suitable carrier.

6. A compound by the name of 1-(3,5-dichloro-pyridin-4-methyl)-5-(indan-2-yloxy)-6-methoxy-2H-phthalazine.

7. A compound by the name of 1-(3,5-dichloro-pyridin-4-methyl)-5-(5-phenyl-pentyl-1-oxy)-6-methoxy-phthalazine.

8. A compound by the name of 6-methoxy-1-phenyl-5-(tetrahydro-furan-2-yloxy)-phthalazine.

* * * * *